(12) United States Patent
Saif et al.

(10) Patent No.: US 12,022,943 B1
(45) Date of Patent: Jul. 2, 2024

(54) HANDS-FREE METHOD OF STORING AND RETRIEVING FOOTWARE

(71) Applicant: Imam Abdulrahman Bin Faisal University, Dammam (SA)

(72) Inventors: Heba Nabil Saif, Dammam (SA); Hala El-Wakeel, Dammam (SA); Asma Alhilal, Dammam (SA); Nourah Almanaa, Dammam (SA); Nouf Altuwaijri, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 18/599,279

(22) Filed: Mar. 8, 2024

Related U.S. Application Data

(60) Continuation of application No. 18/316,491, filed on May 12, 2023, now Pat. No. 11,957,243, which is a division of application No. 17/499,097, filed on Oct. 12, 2021.

(51) Int. Cl.
*A47B 61/04* (2006.01)
*A47B 57/06* (2006.01)
*E05B 69/00* (2006.01)

(52) U.S. Cl.
CPC .............. *A47B 61/04* (2013.01); *A47B 57/06* (2013.01); *E05B 69/003* (2013.01)

(58) Field of Classification Search
CPC ........ A47B 56/06; A47B 61/04; E05B 69/003
See application file for complete search history.

(56) References Cited

U.S. PATENT DOCUMENTS

| | | | |
|---|---|---|---|
| 6,464,142 B1 * | 10/2002 | Denenberg | B65G 1/137 235/462.46 |
| 7,168,905 B1 | 1/2007 | Solomon | |
| 7,689,480 B2 | 3/2010 | Solomon | |
| 8,303,233 B2 | 11/2012 | Solomon | |
| 11,051,613 B1 * | 7/2021 | Gilbreath | E05B 65/46 |
| 11,071,379 B1 * | 7/2021 | Clontz | A47B 61/04 |
| 11,116,314 B1 | 9/2021 | Zhang | |
| 2005/0067420 A1 | 3/2005 | Diaz | |

(Continued)

FOREIGN PATENT DOCUMENTS

| | | |
|---|---|---|
| CN | 209219485 U | 8/2019 |
| CN | 210493233 U | 5/2020 |

(Continued)

*Primary Examiner* — James O Hansen
(74) *Attorney, Agent, or Firm* — Oblon, McClelland, Maier & Neustadt, L.L.P.

(57) ABSTRACT

A shoe organizer unit, a method of using a shoe organizer unit, and a method for storing shoes in a plurality of shoe storing shelves of a shoe organizer unit are described. The shoe organizer unit includes a plurality of shoe storing shelves adapted to store shoes therein. A plurality of linear actuators moves the plurality of shoe storing shelves in a path within a cabinet. A controller manages operation of the linear actuators to move the shoes along the path. Transparent panels secure the shoes within the cabinet. Secure storage and retrieval of the shoes is controlled by electronics including a keypad, a push button and a shoe shelf identification code card printer. The shoe organizer unit provides for sterilization of the shoes stored and secure storing and retrieval of the shoes.

3 Claims, 18 Drawing Sheets

(56) References Cited

U.S. PATENT DOCUMENTS

| | | | |
|---|---|---|---|
| 2007/0090062 A1* | 4/2007 | Girault | A47B 61/04 211/36 |
| 2007/0295580 A1 | 12/2007 | Solomon | |
| 2013/0051959 A1 | 2/2013 | Alghamdi | |
| 2020/0394857 A1 | 12/2020 | Lin | |

FOREIGN PATENT DOCUMENTS

| | | |
|---|---|---|
| CN | 212698135 U | 3/2021 |
| JP | 2000-93238 | 4/2000 |

* cited by examiner

HANDS-FREE METHOD OF STORING AND RETRIEVING FOOTWARE

CROSS-REFERENCE TO RELATED APPLICATIONS

The present application is a Continuation of U.S. application Ser. No. 18/316,491, now allowed, having a filing date of May 12, 2023 which is a Division of U.S. application Ser. No. 17/499,097, pending, having a filing date of Oct. 12, 2021.

BACKGROUND

Technical Field

The present disclosure is directed to a shoe organizer unit, a method of using a shoe organizer unit and a method for storing shoes in a plurality of shoe storing shelves of a shoe organizer unit.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Many public venues require a person to remove his/her shoes before entering, such as nursing homes, hospitals, physical therapy centers, spiritual places (mosques, temples, etc.), yoga classes and spa centers, security check points, and the like. Shoe shelves may be provided, however may not offer secure storage for the shoes. Additionally, removing shoes may be difficult for a person with disabilities.

In order to put on and remove a shoe, a person may sit on a seating area, such as a bench, stool, trunk, or window seat, and place his/her feet on the ground, which may provide an "easy-to-reach" distance for putting on and removing the shoes. However, a seating area is not always available in a public venue. Bending down, even when seated, may cause physical pain or injury to seniors, the overweight and people with injuries or other physical handicaps. For example, a person may fall or stress ribs or internal organs. Other people may feel emotional stress from worrying about how they might be perceived by others while executing such process, especially in public context, which may traumatize their mental health in the long term. Additionally, a person may worry that their shoes may be contaminated by the presence of other shoes or stolen from a shoe retaining area. Further, the process of retrieving the shoes later may be confusing, especially for a person with reduced mobility or mental capacity.

A person may need a convenience tool to aid in putting on and removing shoes. For example, a person may use a shoe remover while taking off a shoe. Shoe removers may take many forms, such as shoe sliders, shoe horns, gripping ropes, assistive sticks, and the like. A person may inset the shoe remover into the shoe to prise the shoe from the foot. Alternatively, a shoe remover may include a recess or other holding mechanism which requires a user to place heel of his/her shoe into the holding mechanism, and then pull his/her foot from the shoe. These devices may help to solve the problem of taking off (or even putting on) the shoe at individual level to some extent; however, they require users to carry a personal shoe remover tool, if there is not one at the public venue A product organizing structure may include shelving which may be used to organize the shoes. For example, Japanese patent application, JP2000093238A, describes a storage apparatus for storing small articles, such as footwear and shoes, which has a belt mechanism to move shelves horizontally and vertically along a circular track. However, the shelves are not adapted with means to grip shoes for during removal, any means to sterilize the footwear, or to provide secure storage and retrieval of the shoes.

U.S. Pat. No. 7,689,480B2 describes a storage module having storage units stacked in multiple rows and columns, each storage unit engaged with the track for selective movement along the track, with wheels and actuators to move the shelves. However, this reference does not mention a shoe receiving area on each shelf or a device which aids the user in removing the shoe, and requires that the user manually places the shoes in the assigned storage unit, which is cumbersome and time consuming.

CN209219485U describes a vertical rotary shoe cabinet having a plurality of shelves and a rotary moving system which raises and lowers the shelves. However, this reference does not mention a shoe receiving area on each shelf having a shoe retainer. The shelves do not provide any means to grip inserted shoes for easy removal or insertion of the foot.

Each of the aforementioned patent references suffers from one or more drawbacks hindering their adoption. Accordingly, it is one object of the present disclosure to provide methods and systems for secure storage of shoes, which provide means for assisting users in the removal of each shoe, sterilizes the shoes and provides easy retrieval of the shoes.

SUMMARY

In an exemplary embodiment, a shoe organizer unit is described. The shoe organizer unit includes a cabinet. The cabinet includes a back wall having a vertical axis and a horizontal axis, a cabinet top, a cabinet bottom, a first side wall, a second side wall, and a central divider. The back wall is separated into a first column by the first side wall and the central divider and a second column by the second side wall and the central divider. The shoe organizer unit further includes a first vertical track positioned on a first inner surface of the first side wall. The shoe organizer unit also includes a second vertical track positioned on a second inner surface of the second side wall. The shoe organizer unit further includes a first horizontal track positioned on the back wall at a location above the cabinet bottom along the horizontal axis. The shoe organizer unit also includes a second horizontal track positioned on the back wall beneath the cabinet top along the horizontal axis. The shoe organizer unit further includes a plurality of shoe storing shelves, each shoe storing shelf includes a first projection configured to engage with the first vertical track and a second projection configured to engage with the second vertical track, and a slider hook configured to engage with either the first horizontal track or the second horizontal track. The shoe organizer unit further includes a plurality of linear actuators configured to move each one of the plurality of shoe storing shelves in a path along the first vertical track, the first horizontal track, the second vertical track and the second horizontal track. The shoe organizer unit further includes a base surface of each shoe storing shelf divided into a left base surface and a right base surface. Herein, each shoe storing shelf includes a left shoe retainer positioned on the left base surface and a right shoe retainer positioned on the right base surface.

In another exemplary embodiment, a method of using a shoe organizer unit is described. The method includes storing a pair of shoes in the shoe organizer unit. Storing the pair of shoes in the shoe organizer unit includes inserting a first shoe into a first shoe retainer of a shoe storing shelf. Herein, the shoe storing shelf is located in a shoe reception area of the shoe organizer unit. Storing the pair of shoes in the shoe organizer unit further includes removing the first shoe by twisting the first shoe against a first pair of retractable pillars located in the first shoe retainer. Storing the pair of shoes in the shoe organizer unit further includes inserting a second shoe into a second shoe retainer of the shoe storing shelf and removing the second shoe by twisting the second shoe against a second pair of retractable pillars located in the second shoe retainer. Storing the pair of shoes in the shoe organizer unit further includes receiving a shoe shelf identification code from a keypad located on the shoe organizer unit. The keypad is operatively connected to a controller which generates the shoe shelf identification code and stores the shoe shelf identification code in a memory. Storing the pair of shoes in the shoe organizer unit further includes pressing an actuator switch to move the shoe storing shelf upwards into a sealed area of the shoe organizer unit. The method further includes retrieving the pair of shoes from the shoe organizer unit. Retrieving the pair of shoes from the shoe organizer unit includes inputting the shoe shelf identification code into the keypad. Herein, the controller matches the shoe shelf identification code to the shoe shelf identification code stored in the memory. The controller further provides power to a plurality of linear actuators to move the shoe storing shelf into a shoe reception area of the shoe organizer unit. Retrieving the pair of shoes from the shoe organizer unit further includes removing the first shoe from the first shoe retainer and the second shoe from the second shoe retainer.

In another exemplary embodiment, a method for storing shoes in a plurality of shoe storing shelves of a shoe organizer unit is described. The shoe organizer unit includes a cabinet. The method includes moving, by a first linear actuator, a first shoe storing shelf along a first horizontal track from a base of a first column of the cabinet to a shoe reception area located at a base of a second column of the cabinet. The method further includes retracting the first linear actuator. The method further includes inserting a first shoe into a first shoe retainer of the first shoe storing shelf. The method further includes removing the first shoe by twisting the first shoe against a first pair of retractable pillars located in the first shoe retainer. Herein, the first pair of retractable pillars is configured to press against the first shoe. The method further includes inserting a second shoe into a second shoe retainer of the first shoe storing shelf. The method further includes removing the second shoe by twisting the second shoe against a second pair of retractable pillars located in the second shoe retainer. Herein, the second pair of retractable pillars is configured to press against the second shoe. The method further includes raising the first shoe storing shelf by a second linear actuator. Herein, a first projection located on a first side of the first shoe storing shelf engages with a fourth vertical track located on an inner surface of a central divider of the cabinet. Herein, a first plurality of shoe storing shelves are vertically stacked one above the other in the second column and are configured to sequentially move in an upward direction when the second linear actuator raises each shoe storing shelf in the shelf reception area into the second column. The method further includes moving a first support actuator to support a first projection located on a first side of the first shoe storing shelf. The method further includes retracting the second linear actuator. The method further includes moving, by a third linear actuator, a top shoe storing shelf of the first plurality of shoe storing shelves upwards such that a slider hook on a backside of the top shoe storing shelf engages with a second horizontal track located at a top of the second column. The method further includes moving, by a fourth linear actuator, the top shoe storing shelf from the second column to the first column to rest upon a second plurality of shoe storing shelves which are vertically stacked one above the other in the first column and which are configured to sequentially move in a downward direction in the first column. The method further includes moving, by a fifth linear actuator, the top shoe storing shelf downward such that the slider hook on the backside of the top shoe storing shelf disengages from the second horizontal track. Herein, a bottom shoe storing shelf of the first column engages with a second support actuator. The method further includes releasing the second support actuator and moving, by a sixth linear actuator, the bottom shoe storing shelf of the first column to engage with the first horizontal track when the first shoe storing shelf is in the shoe reception area.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
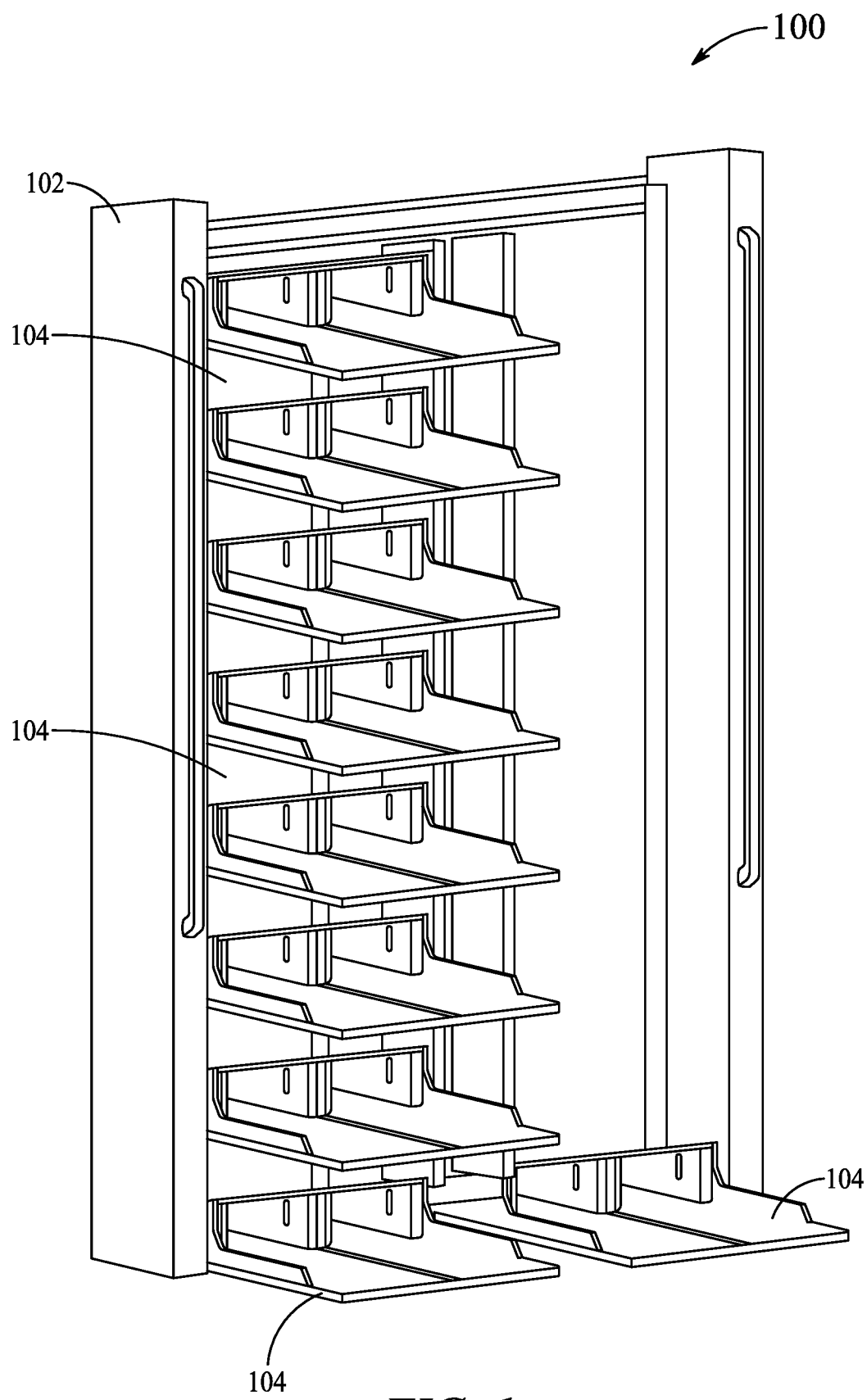
FIG. 1 is a perspective view of a shoe organizer unit, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a shoe organizer unit, a method of using a shoe organizer unit and a method for storing shoes in a plurality of shoe storing shelves of a shoe organizer unit. The shoe organizer unit assists users to overcome the obstacles of taking off and organizing their shoes by aiding in the shoe removal process, ensuring secure storage of the removed shoes, sterilization of the shoes, and easy retrieval of the shoes.

Referring to FIG. 1, a perspective view of a shoe organizer unit 100 is illustrated. The shoe organizer unit 100 provides space for storing the shoes. The shoe organizer unit 100 includes an automated mechanism for efficient storing, organizing and retrieval of shoes stored therein. The shoe organizer unit 100 can aid a person who suffers from a physical body limitation to easily take off his/her shoes without the need to bend down. The shoe organizer unit 100 has an inclusive design to support people, especially those suffering from disabilities, with shoe removal and reinstalling the shoes, as well as shoe organizing functions. The shoe organizer unit 100 is designed to be used at public places like nursing homes, hospitals, physical therapy centers, spiritual places (mosques, temples, etc.), yoga classes and spa centers, security check points, and all similar places where a person's shoes need to be removed. The shoe organizer unit can further be used in private residences for individuals in need. In general, the present shoe organizer unit 100 may be used in any place where there is a need to store and/or organize shoes. Herein, the term "shoes" is meant to incorporate any kind of footwear, including boots, sandals, slippers, clogs, etc. without any limitations.

The shoe organizer unit 100 includes a cabinet 102. The cabinet 102 is designed to be supported on a floor or any planar surface. The cabinet 102 may be designed to have a sufficient volume to allow for required number of shoes to be stored in the shoe organizer unit 100. The shoe organizer unit 100 further includes a plurality of shoe storing shelves 104. Each of the shoe storing shelves 104 is adapted to accommodate and store one pair of shoes therein. The shoe storing shelves 104 are adapted to move within the cabinet 102 to allow for efficient storage of shoes in the shoe organizer unit 100. The number of the shoe storing shelves 104 that may be incorporated in the shoe organizer unit 100 may depend on the volume of the cabinet 102. It may be appreciated that larger the volume of the cabinet 102, the greater the number of shoe storing shelves 104 that may be incorporated therein, and thus more shoes may be stored in the shoe organizer unit 100. Therefore, depending on the application of the shoe organizer unit 100, the volume of the cabinet 102 and the number of shoe storing shelves 104 may be selected. For example, a public venue may have a plurality of shoe organizer units, however, a private home shoe storage unit catering to individual or family needs, may be smaller and have fewer shelves as compared to a public space catering to tens or even hundreds of people.

Figure 2A:
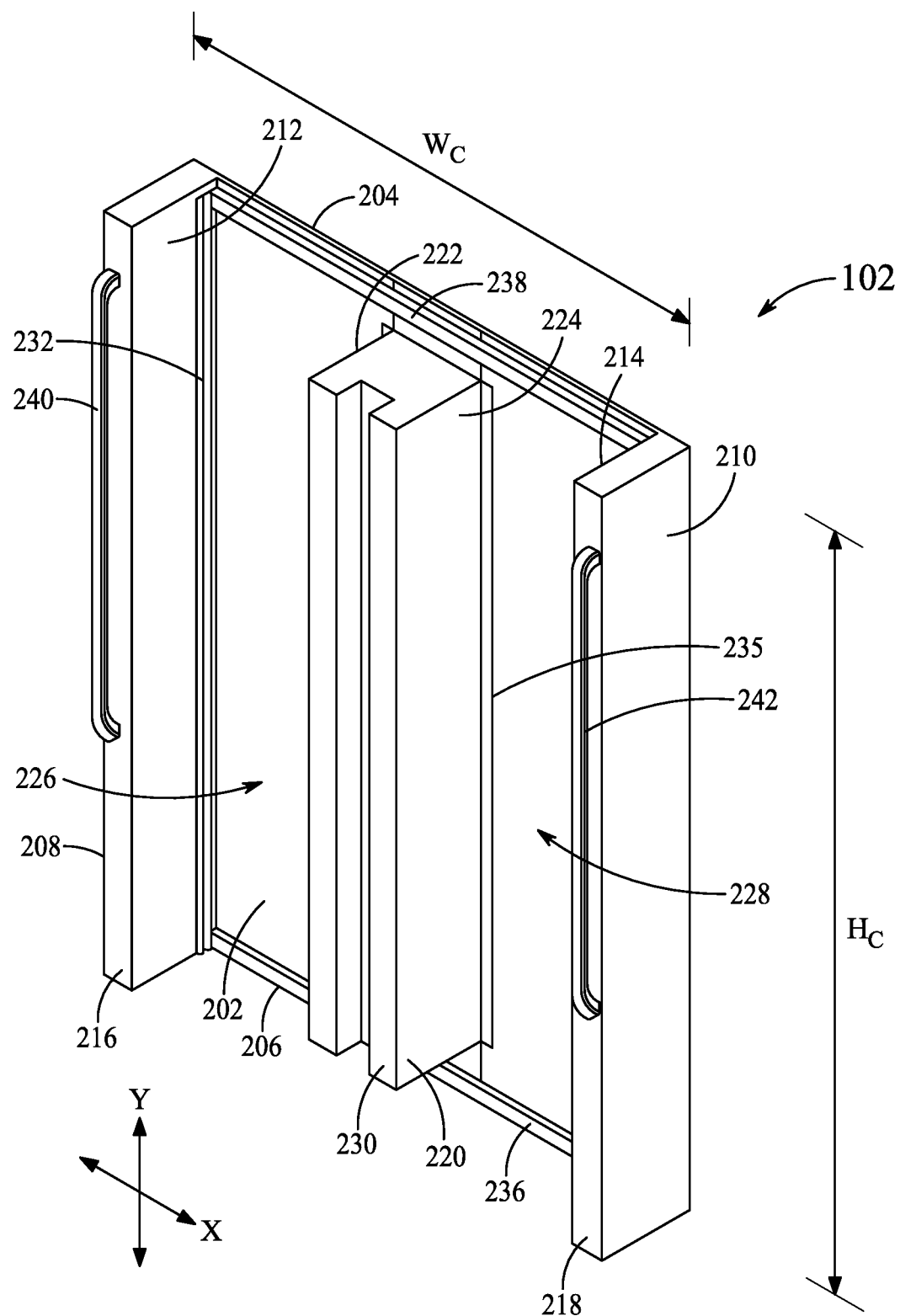
FIG. 2A is a perspective view of a cabinet of the shoe organizer unit, according to certain embodiments.
Figure 2B:
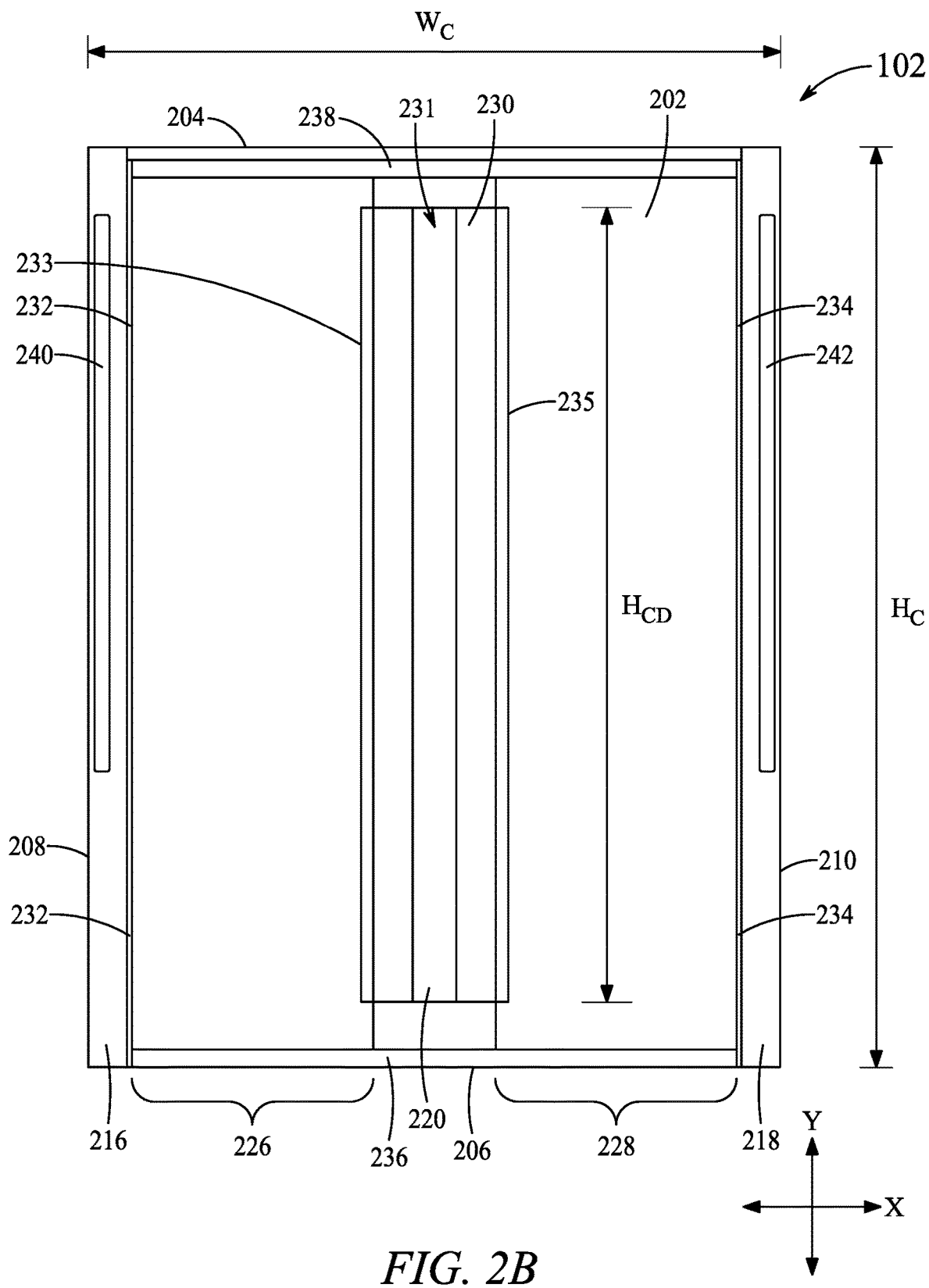
FIG. 2B is a front view of the cabinet of FIG. 2A, according to certain embodiments.
Figure 2C:
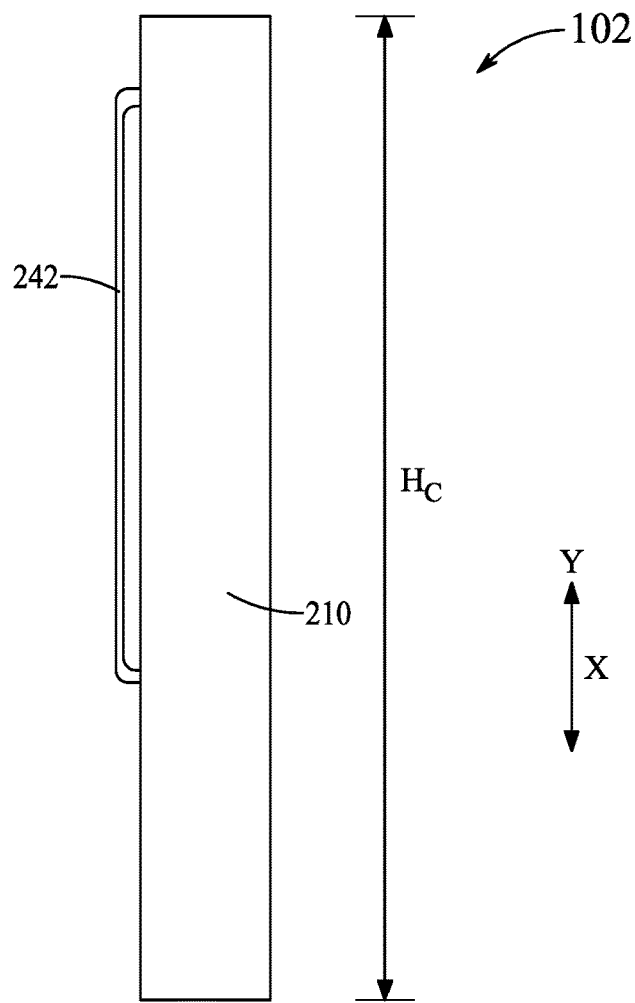
FIG. 2C is a side view of the cabinet of FIG. 2A, according to certain embodiments.
Figure 2D:
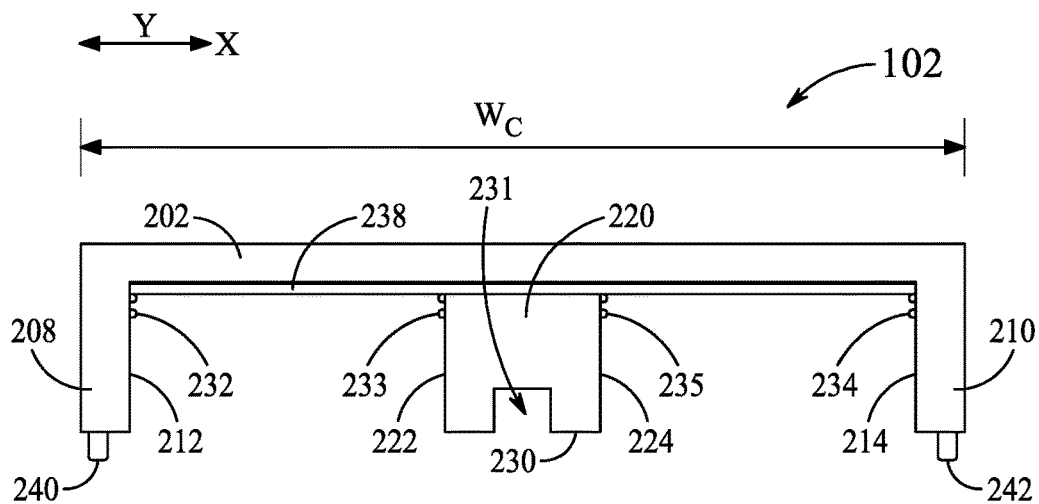
FIG. 2D is a top view of the cabinet of FIG. 2A, according to certain embodiments.

Referring to FIG. 2A, a perspective view of the cabinet 102 of the shoe organizer unit 100 is illustrated. FIG. 2B illustrates a front view of the cabinet 102 of FIG. 2A, FIG. 2C illustrates a side view of the cabinet 102 of FIG. 2A, and FIG. 2D illustrates a top view of the cabinet 102 of FIG. 2A. Referring to FIGS. 2A to 2D in combination, the cabinet 102 may generally have a cuboidal shape. In an example, the cabinet 102 may be formed of any one of wood, plywood, laminated sheets, or the like. In another example, the cabinet 102 may be formed of plastic or the metallic materials which provide structural integrity. The cabinet 102 includes a back wall 202 having a vertical axis 'Y' and a horizontal axis 'X'. The back wall 202 may generally be a planar structure, extending along the vertical axis 'Y' in one direction to define a height '$H_C$' of the cabinet 102 and the horizontal axis 'X' in another direction to define a width '$W_C$' of the cabinet 102. The cabinet 102 also includes a cabinet top 204 and a cabinet bottom 206. The cabinet top 204 is defined by an uppermost portion or an upper edge of the cabinet 102, and the cabinet bottom 206 is defined by a lowermost portion or a lower edge of the cabinet 102. The cabinet top 204 may generally be located higher up (from the ground or a supporting surface of the cabinet 102) along the vertical axis 'Y' as compared to the cabinet bottom 206.

The cabinet 102 further includes a first side wall 208 and a second side wall 210. The first side wall 208 and the second side wall 210 are disposed along the horizontal axis 'X' and define side edges of the cabinet 102. The first side wall 208 has a first inner surface 212 and the second side wall 210 has a second inner surface 214, with the first inner surface 212 and the 20 second inner surface 214 facing towards a center of the cabinet 102 along the horizontal axis 'X'. The first side wall 208 and the second side wall 210 may extend to a height along the vertical axis 'Y' generally equal to the height '$H_C$' of the cabinet 102. The first side wall 208 and the second side wall 210 may protrude outwardly from the back wall 202 to define their respective front surfaces, i.e., a first front surface 216 of the first side wall 208 and a second front surface 218 of the second side wall 210.

The cabinet 102 further includes a central divider 220. In the cabinet 102, the central divider 220 protrudes outwardly from the back wall 202, in a same direction as the first side wall 208 and the second side wall 210. The central divider 220 has a first inner surface 222 facing the first side wall 208 and a second inner surface 224 facing the second side wall 210, along the horizontal axis 'X'. The central divider 220 is disposed substantially at a center of the width '$W_C$' of the cabinet 102. The back wall 202 is separated into a first column 226 by the first side wall 208 and the central divider 220, and a second column 228 by the second side wall 210 and the central divider 220. As discussed, with the central divider 220 is generally disposed along the center of the width '$W_C$' of the cabinet 102, so that the first column 226 and the second column 228 may have generally equal widths. In the present examples, the central divider 220 has a height '$H_{CD}$' along the vertical axis 'Y' less than the height '$H_C$' of the cabinet 102. The central divider 220 may be positioned along the vertical axis 'Y' to have a gap from the cabinet top 204 as well as a gap from the cabinet bottom 206. These gaps may be at least slightly greater than a height of the shoe storing shelf 104, in order to allow for the shoe storing shelf 104 to move horizontally (along the horizontal axis 'X') from the first column 226 to the second column 228 and vice-versa, in the shoe organizer unit 100 (as discussed later in the description). In a non-limiting example, such gaps may be about 2 feet; however, in other non-limiting examples, such gaps may be greater or less than 2 feet as long as the shoe storing shelf 104 is able to freely travel therethrough without obstruction. As discussed, the central divider 220 protrudes outwardly from the back wall 202 and thereby defines a front surface 230. The front surface 230, in the central divider 220, may be used to support or accommodate various components of the shoe organizer unit 100, as discussed later in the description. The central divider 220 extends along the horizontal axis 'X' (as may be seen from FIG. 2B). As better seen with respect to FIG. 2B and FIG. 2D, the central divider 220 may have a generally U-shaped cross-section to define an extrusion in the front surface 230, extending along the height '$H_{CD}$' thereof, which may house the said various components of the shoe organizer unit 100.

Referring again to FIGS. 2A-2D in combination, the shoe organizer unit 100 includes a first vertical track 232 positioned on the first inner surface 212 of the first side wall 208. The shoe organizer unit 100 also includes a second vertical track 234 (as shown in FIG. 2B and FIG. 2D) positioned on the second inner surface 214 of the second side wall 210. Specifically, the first vertical track 232 and the second vertical track 234 may be disposed proximal to a first corner between the first inner surface 212 and the back wall 202 of the cabinet 102, and a second corner between the second inner surface 214 and the back wall 202 of the cabinet 102, respectively. The first vertical track 232 and the second vertical track 234 may extend along the vertical axis 'Y' for the entire height '$H_C$' of the cabinet 102 (as shown in FIG. 2B). In some examples, the shoe organizer unit 100 further includes a third vertical track 233 positioned on the first inner surface 222 of the central divider 220. The shoe organizer unit 100 also includes a fourth vertical track 235 positioned on the second inner surface 224 of the central divider 220. The third vertical track 233 and the fourth vertical track 235 may extend along the vertical axis 'Y' for the entire height '$H_C$' of the cabinet 102, similar to the first vertical track 232 and the second vertical track 234 (as shown in FIG. 2B). The shoe organizer unit 100 further includes a first horizontal track 236 positioned on the back wall 202 at a location above the cabinet bottom 206 along the horizontal axis 'X' and a second horizontal track 238 positioned on the back wall 202 beneath the cabinet top 204 along the horizontal axis 'X'. By the term "beneath", it is meant that the second horizontal track 238 is positioned at a location below the cabinet top 204 along the horizontal axis 'X'. The first horizontal track 236 and the second horizontal track 238 may extend along the horizonal axis 'X' for the entire width '$W_C$' of the cabinet 102 between the first side wall 208 and the second side wall 210. In the present examples, the first vertical track 232, the second vertical track 234, the first horizontal track 236 and the second horizontal track 238 may be in the form of channels to allow for movement (sliding) of the shoe storing shelves 104 thereon when engaged therewith, as discussed later in the description. In one or more examples, the tracks 232, 234, 236, 238 may be made of aluminum, steel, or any other similar material which can provide structure and low friction sliding of the shoe storing shelves 104 (as discussed later) when installed therein.

Furthermore, the shoe organizer unit 100 includes a first hand rail 240 located on the first front surface 216 of the first side wall 208 along the vertical axis 'Y', and a second hand rail 242 located on the second front surface 218 of the second side wall 210 along the vertical axis 'Y'. In one or more examples, the first hand rail 240 and the second hand rail 242 may be made of coated metal. In an example, the first hand rail 240 and the second hand rail 242 may be fastened to a planar surface as provided by the first front surface 216 of the first side wall 208 and the second front surface 218 of the second side wall 210, respectively. The first hand rail 240 and the second hand rail 242 may be in the form of elongate members provided on the first side wall 208 and the second side wall 210, respectively, of the cabinet 102, to be used by a user for support purposes when using the shoe organizer unit 100 for removing or putting on the shoes. It may be appreciated that although the first hand rail 240 and the second hand rail 242 are shown to be elongate members, the first hand rail 240 and the second hand rail 242 may alternatively be in the form of a handle, a knob, or the like without departing from the spirit and the scope of the present disclosure.

Figure 3A:
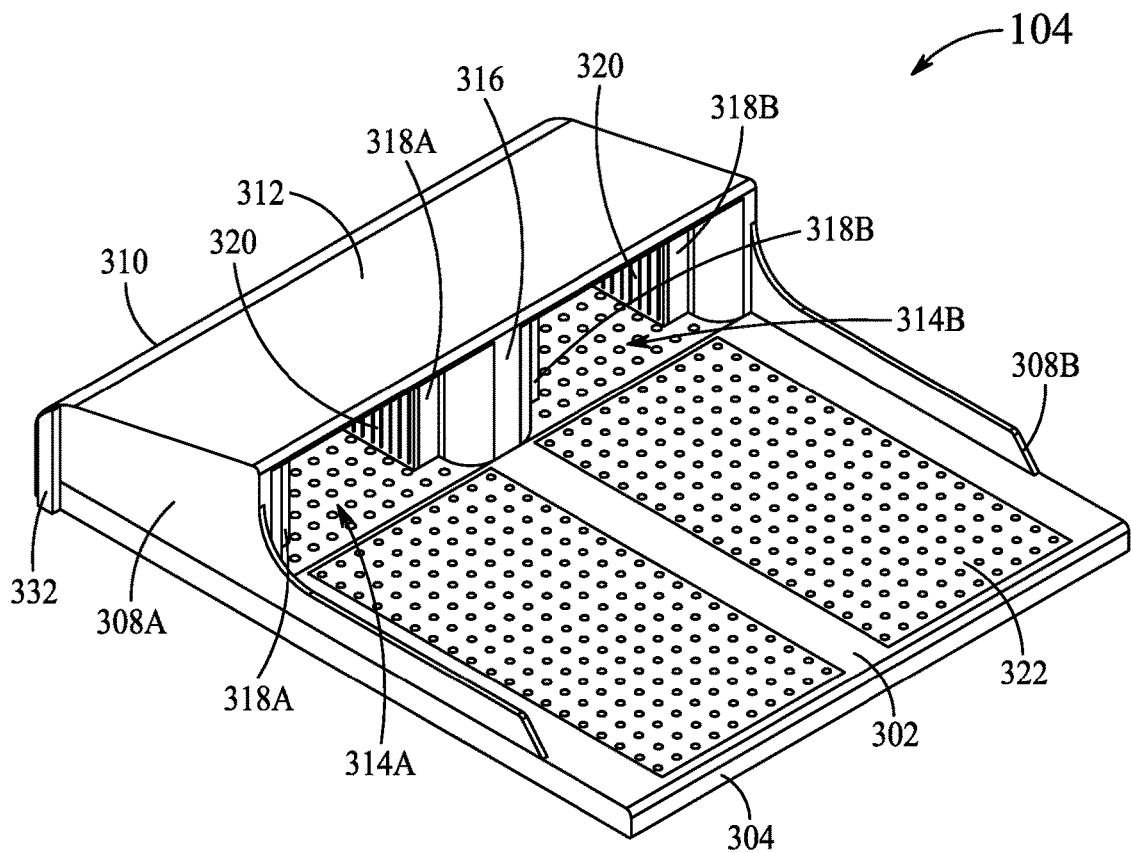
FIG. 3A is a perspective view of a shoe storing shelf of the shoe organizer unit, according to certain embodiments.
Figure 3B:
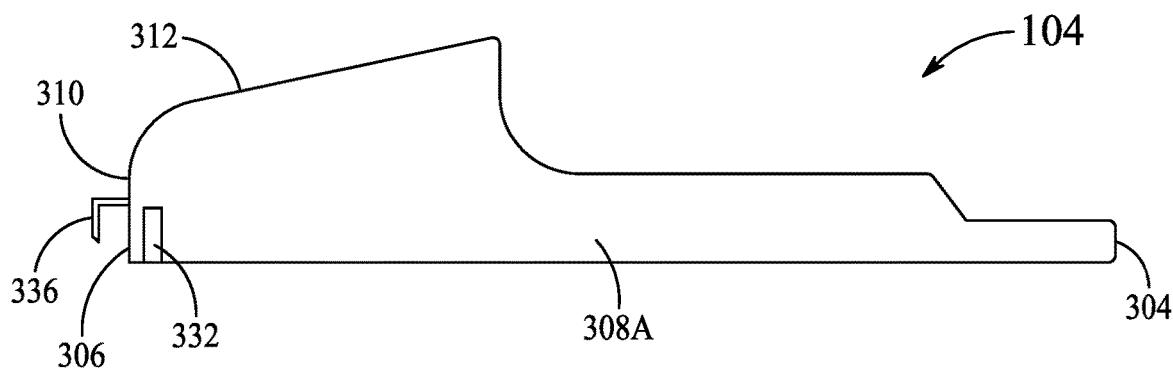
FIG. 3B is a side view of the shoe storing shelf of FIG. 3A, according to certain embodiments.
Figure 3C:
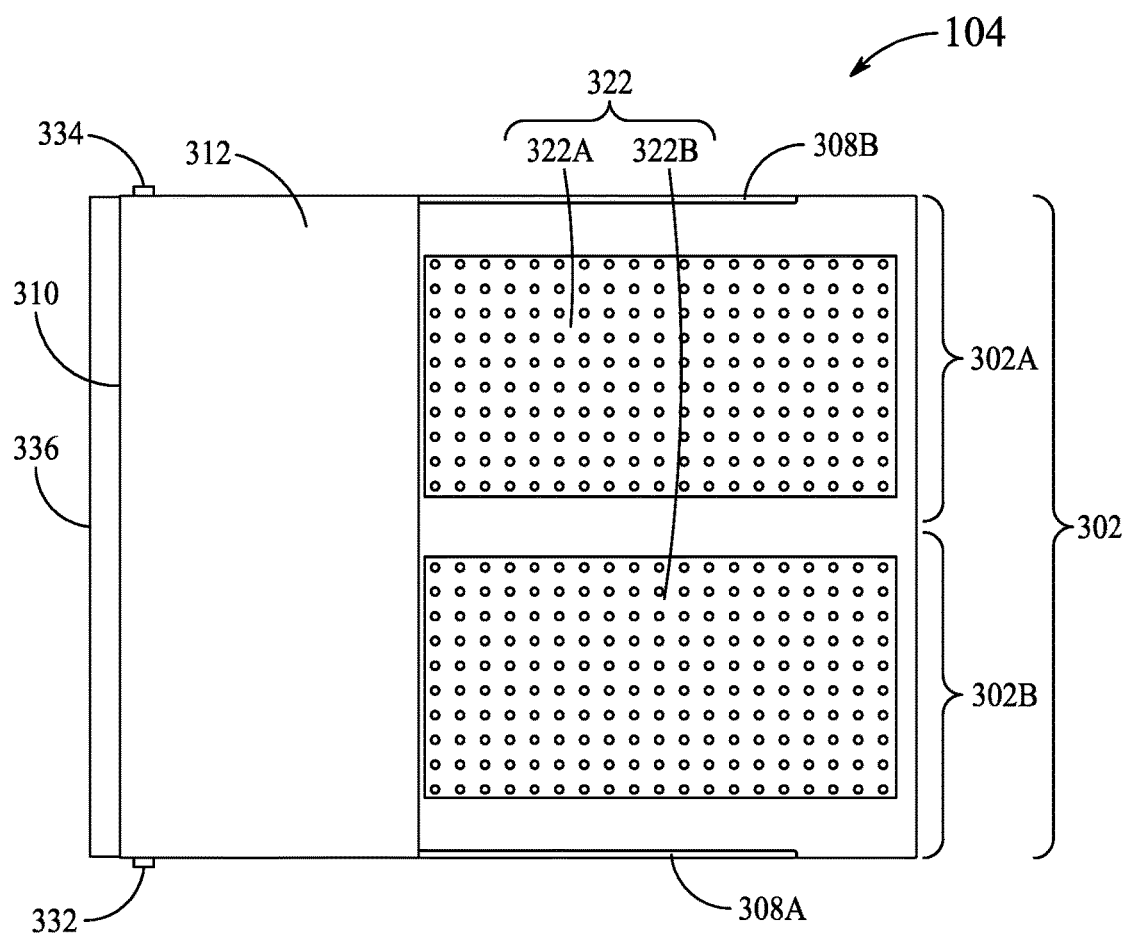
FIG. 3C is a top view of the shoe storing shelf of FIG. 3A, according to certain embodiments.
Figure 3D:
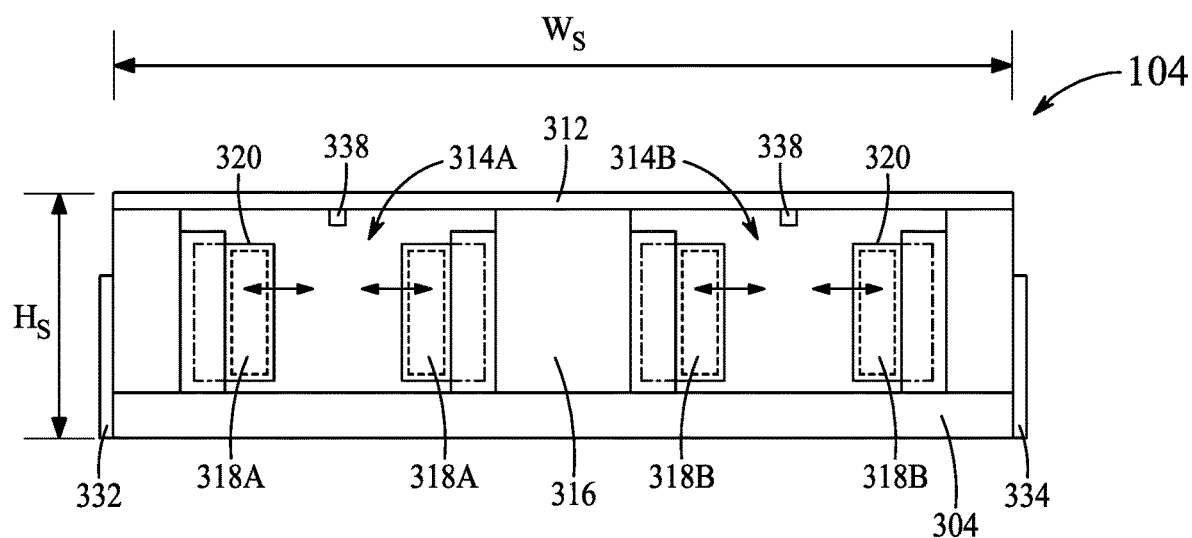
FIG. 3D is a front view of the shoe storing shelf of FIG. 3A, according to certain embodiments.

Referring to FIG. 3A, a perspective view of the shoe storing shelf 104 of the shoe organizer unit 100 is illustrated. FIG. 3B illustrates a side view of the shoe storing shelf 104 of FIG. 3A, FIG. 3C illustrates a top view of the shoe storing shelf 104 of FIG. 3A, and FIG. 3D illustrates a front view of the shoe storing shelf 104 of FIG. 3A. Referring to FIGS. 3A to 3D in combination, as may be seen, the shoe storing shelf 104 (sometimes referred to as "shoe shelf 104") has a generally cuboidal shape, with a height '$H_S$' of the shoe storing shelf 104 significantly smaller as compared to the height '$H_C$' of the cabinet 102. This allows multiple shoe storing shelves 104 to be stacked vertically in the cabinet 102 (as shown in FIG. 1). Further, a width '$W_S$' of the shoe storing shelf 104 (as shown in FIG. 3D) is significantly smaller as compared to the width '$W_C$' of the cabinet 102, generally equal to width of the columns 226, 228 therein. Thus, the shoe storing shelves 104 may be supported within any one of the first column 226 and the second column 228 in the cabinet 102. It may be appreciated that although in the present illustrations, the cabinet 102 is shown to include two columns 226, 228; in other examples, the cabinet 102 may have more than two columns, including three or four columns without departing from the scope and the spirit of the present disclosure. It may be contemplated that in such case, the number of the shoe storing shelves 104 that may be incorporated in the cabinet 102 may increase, thereby increasing the number of shoes that may be stored in the shoe organizer unit 100.

The shoe storing shelf 104 includes a base surface 302. The base surface 302 has a front edge 304 and a rear edge 306. Further, the shoe storing shelf 104 includes two side walls, a left side wall 308A (sometimes referred to as "first side 308A") and a right side wall 308B (sometimes referred to as "second side 308B"), extending upwardly from the base surface 302. In an example, as illustrated, the side walls 308A, 308B may extend from the rear edge 306, toward the front edge 304. In an example, as best illustrated in FIG. 3A and FIG. 3B, the side walls 308A, 308B may extend partly, with varying height, from the rear edge 306, toward the front edge 304. In an alternate example, the side walls 308A, 308B may extend with consistent height from the rear edge 306 toward the front edge 304. The shoe storing shelf 104 also includes a backside 310 extending upwardly from the base surface 302 at the rear edge 306 thereof. The shoe storing shelf 104 further includes an upper surface 312 which is supported over the backside 310 and the side walls 308A, 308B.

As discussed, the shoe storing shelf 104 is designed to accommodate a pair of shoes including a left shoe and a right shoe. For this purpose, the base surface 302 of the shoe storing shelf 104 is divided into a left base surface 302A and a right base surface 302B (as shown in FIG. 3C). Further, the shoe storing shelf 104 includes a left shoe retainer 314A (sometimes also referred to as first shoe retainer 314A) positioned on the left base surface 302A and a right shoe retainer 314B (sometimes also referred to as second shoe retainer 314B) positioned on the right base surface 302B. In the present examples, the left shoe retainer 314A and the right shoe retainer 314B are defined by a center wall 316 extending upwardly from the base surface 302, between the left base surface 302A and the right base surface 302B. Herein, the left shoe retainer 314A positioned on the left base surface 302A is designed to accommodate the left shoe (first shoe) and the right shoe retainer 314B positioned on the right base surface 302B is designed to accommodate the right shoe (second shoe); although, it may be appreciated that, generally, the left shoe retainer 314A and the right shoe retainer 314B may have similar shape and design for the purposes of the present disclosure.

In particular, the left shoe retainer 314A includes a first pair of retractable pillars 318A. Each retractable pillar 318A is configured to retract in an outward direction when a shoe (such as, the left shoe) is inserted into the left shoe retainer 314A. Herein, by "outward direction" it is meant that the two retractable pillars 318A, of the first pair of retractable pillars 318A, are adapted to retract in respective outward direction away from the shoe inserted therein, with the respective outward directions being opposite for the two retractable pillars 318A along the horizontal axis 'X' of the cabinet 102 when positioned therein. The retractable pillars 318A are configured to grip the shoe, such as the left shoe inserted therebetween. Similarly, the right shoe retainer 314B includes a second pair of retractable pillars 318B. Each retractable pillar 318B is configured to retract in an outward direction when a shoe (such as, the right shoe) is inserted into the right shoe retainer 314B. Herein, by "outward direction" it is meant that the two retractable pillar 318B, of the second pair of retractable pillars 318B, are adapted to retract in respective outward direction away from the shoe inserted therein, with the respective outward directions being opposite for the two retractable pillars 318B along the horizontal axis 'X', in order to accommodate different widths of shoes. The retractable pillars 318B are configured to grip the shoe inserted therebetween.

Figure 7A:
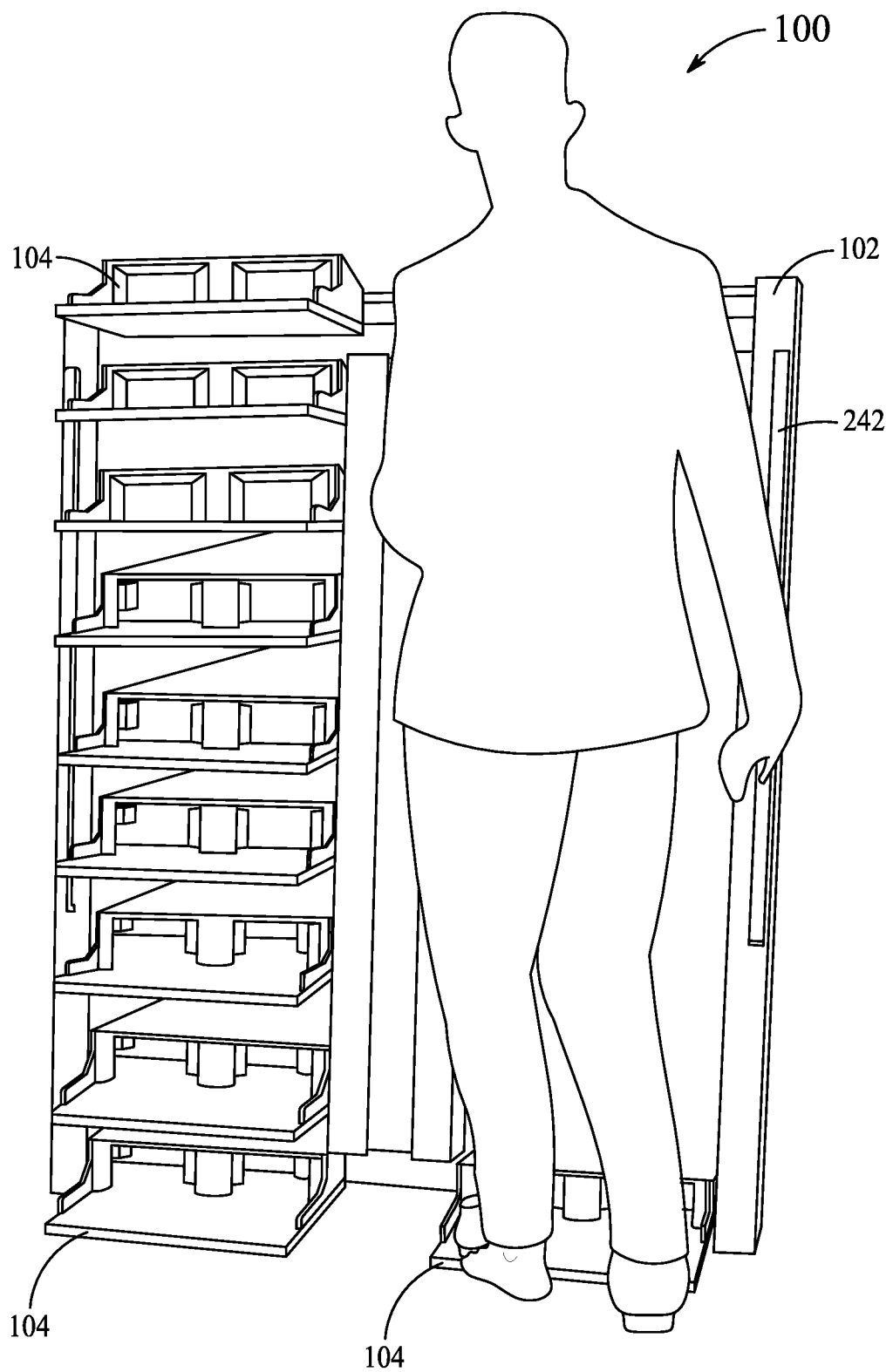
FIG. 7A is a diagrammatic illustration of a step involved in using the shoe organizer unit of FIG. 1, according to certain embodiments.
Figure 7B:
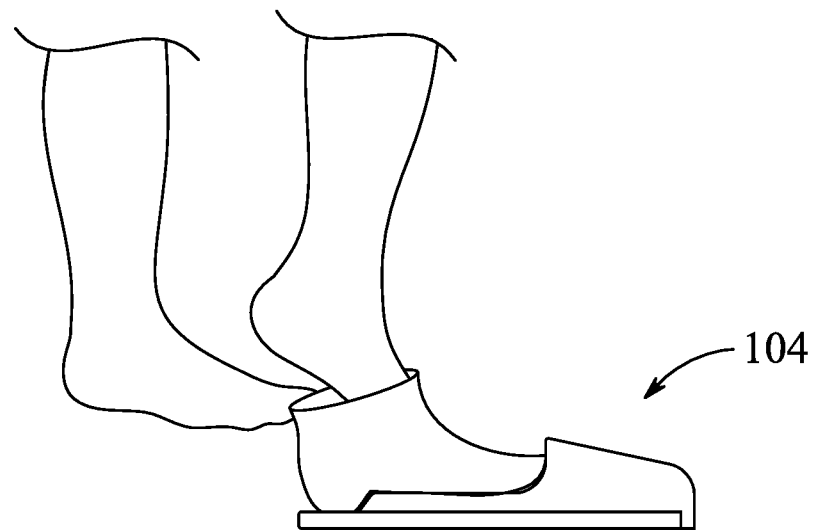
FIG. 7B is a diagrammatic illustration of a step involved in using the shoe storing shelf of FIG. 3A, according to certain embodiments.
Figure 7C:
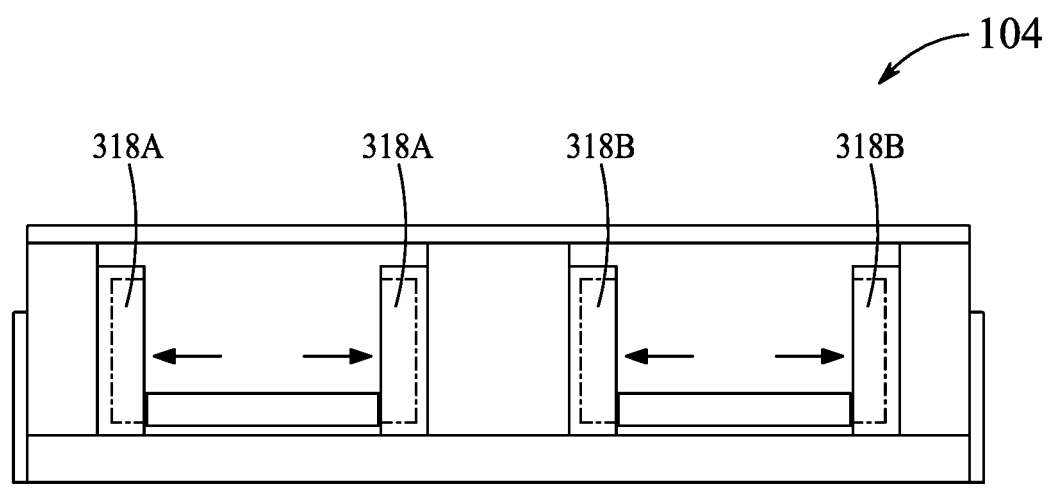
FIG. 7C is a diagrammatic illustration of a step involved in using the shoe storing shelf of FIG. 3A, according to certain embodiments.

Each retractable pillar 318A, 318B includes an elastic adjustable covering 320 configured to grip a sole of the shoe inserted between the retractable pillars 318A, 318B. Specifically, the elastic adjustable covering 320 of each retractable pillar 318A, 318B grips a toe cap portion of the shoe inserted in the corresponding shoe retainer 314A, 314B. In an example, the elastic adjustable covering 320 may be made of soft rubber or the like. The adjustable covering 320 may include frictional gripping features, such as a textured surface. In an aspect of the present disclosure, as better shown in FIG. 3D, the retractable pillars 318A, 318B are in the form of slats, where the slats are connected to springs (not shown) which compress the slats against the shoe inserted in the respective shoe retainers 314A, 314B. It may be appreciated that the retractable pillars 318A, 318B may retract (as depicted in FIG. 7C) due to a force generated by pushing of the shoe inwards into the left shoe retainer 314A by the user of the shoe organizer unit 100 and thereby grip the shoe due to cushioning provided by the elastic adjustable covering 320. The retractable pillars 318A, 318B may return back to their original configuration (as depicted in FIG. 3D) when the shoe is removed due to pulling of the shoe outwards from the left shoe retainer 314A by the user of the shoe organizer unit 100. In a non-limiting example, the retractable pillars 318A, 318B may be connected to springs which return them to their original configuration when the shoe is removed. Other possible configurations or mechanisms for the retractable pillars 318A, 318B for the purpose of gripping the shoe may be contemplated without departing from the spirit and the scope of the present disclosure.

The shoe organizer unit 100, or specifically the shoe storing shelf 104, further includes a textured rubber mat 322 located on the left base surface 302A and the right base surface 302B. In an example, the textured rubber mat 322 may be a single piece placed over entire of the base surface 302, and may have textured regions corresponding to the left base surface 302A and the right base surface 302B. In another example, as best shown in FIG. 3C, the textured rubber mat 322 may include two separate textured rubber mats 322A, 322B provided with textured regions, with the textured rubber mat 322A placed on the left base surface 302A and the textured rubber mat 322B placed on the right base surface 302B. The textured rubber mat 322 is configured to provide friction when withdrawing a foot from a shoe, such as the shoe gripped by the retractable pillars 318A, 318B in the shoe retainers 314A, 314B of the shoe storing shelf 104. This, in turn, may help the user to easily remove or put on the shoes, when using the shoe organizer unit 100 of the present disclosure.

Further, as shown in FIG. 3B, each shoe storing shelf 104 includes a first projection 332 configured to engage with the first vertical track 232 and a second projection 334 configured to engage with the second vertical track 234. In the present examples, the first projection 332 and the second projection 334 are in form of protrusions extending outwardly from the left side wall 308A and the right side wall 308B, respectively, of the shoe storing shelf 104. It may be appreciated that when the shoe storing shelf 104 is disposed in the first column 226, the shoe storing shelf 104 may be engaged with the first vertical track 232 at the first projection 332 and the third vertical track 233 at the second projection 334; and when the shoe storing shelf 104 is disposed in the second column 228, the shoe storing shelf 104 may be engaged with the fourth vertical track 235 at the first projection 332 and the second vertical track 234 at the second projection 334. The shoe storing shelf 104 also includes a slider hook 336 configured to engage with either the first horizontal track 236 or the second horizontal track 238. Particularly, with the first horizontal track 236 and the second horizontal track 238 having similar design, the slider hook 336 is designed to engage with any one of the first horizontal track 236 and the second horizontal track 238, and engages with one of the first horizontal track 236 and the second horizontal track 238 at any given instance. In the present examples, the slider hook 336 is in the form of a L-shaped hook extending outwardly from the backside 310 of the shoe storing shelf 104.

In some examples, as shown in FIG. 3D, each shoe storing shelf 104 includes a proximity sensor 338 located on one of the upper surface 312 of the left shoe retainer 314A and the right shoe retainer 314B. In an example, the proximity sensor 338 is located on the upper surface 312 corresponding to one of the left shoe retainer 314A and the right shoe retainer 314B. In another example, two proximity sensors 338 may be provided, with one located on the upper surface 312 corresponding to the left shoe retainer 314A and other on the upper surface 312 corresponding to the right shoe retainer 314B. The proximity sensor 338 is configured to detect the insertion of the shoe in corresponding one or both of the left shoe retainer 314A and the right shoe retainer 314B.

Figure 4A:
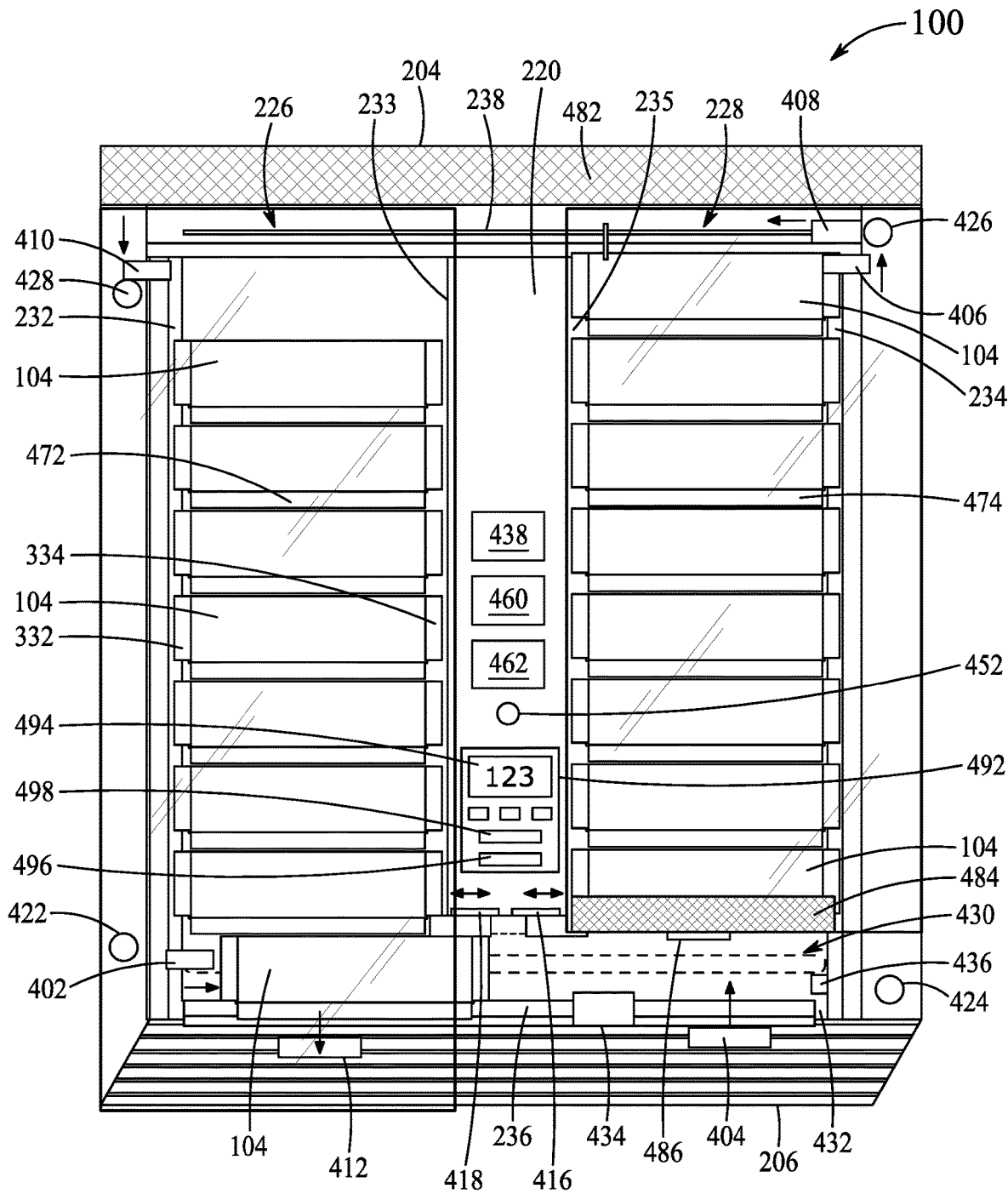
FIG. 4A is a front view of the shoe organizer unit, according to certain embodiments.
Figure 4B:
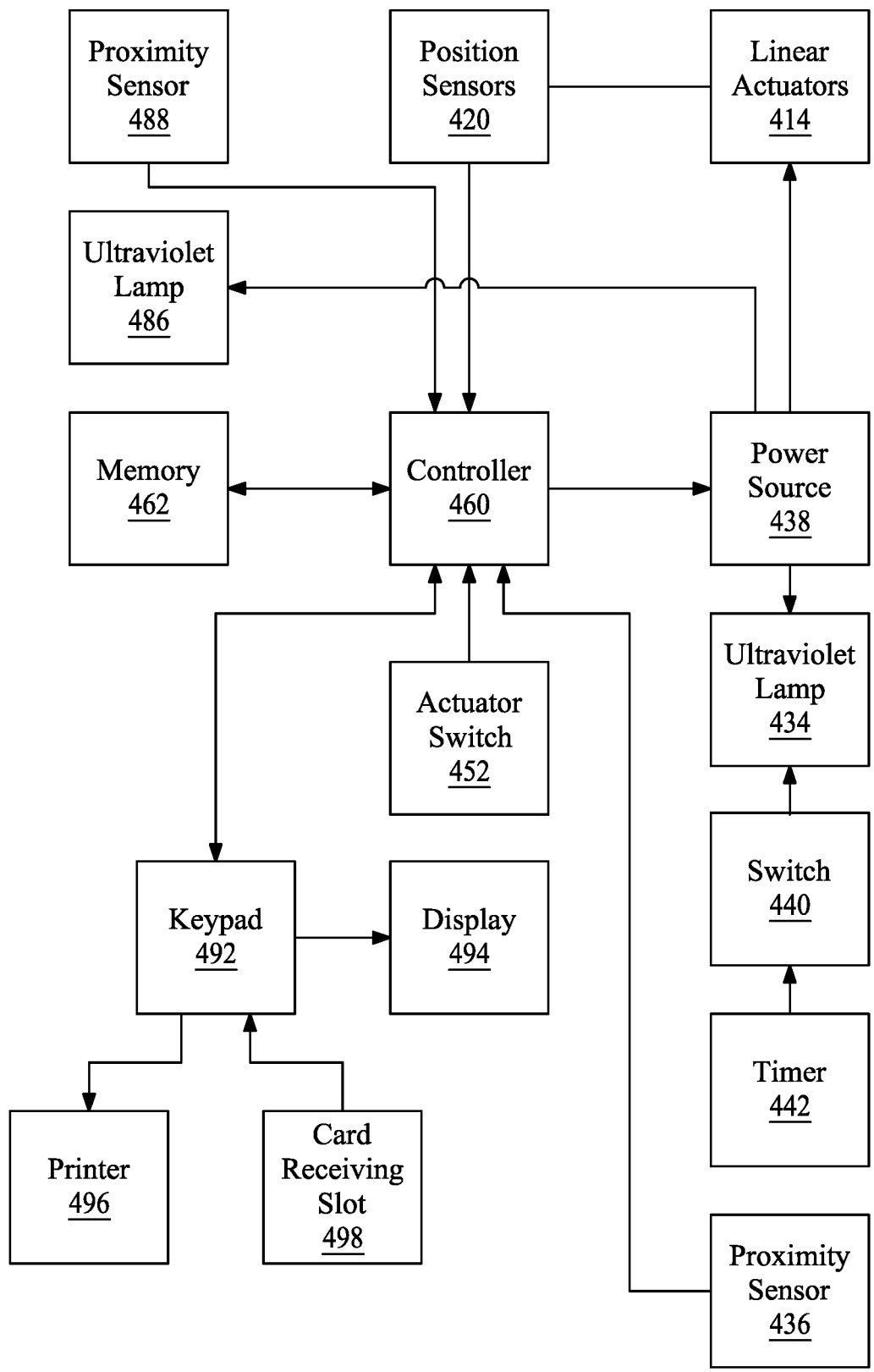
FIG. 4B is a block diagram of a circuit for the shoe organizer unit, according to certain embodiments.

Referring to FIG. 4A, a front view of the shoe organizer unit 100 is illustrated. FIG. 4B is a block diagram of a circuit for the shoe organizer unit 100. Particularly, the circuit of FIG. 4B shows connections between various mechanical, electrical and electro-mechanical components in the shoe organizer unit 100. Referring to FIG. 4A and FIG. 4B in combination, the shoe organizer unit 100 includes a plurality of linear actuators configured to move each one of the plurality of shoe storing shelves 104 in a path along the first vertical track 232, the first horizontal track 236, the second vertical track 234 and the second horizontal track 238. Particularly, the shoe organizer unit 100 includes a first linear actuator 402 associated with the first horizontal track 236, a second linear actuator 404 associated with the second vertical track 234, a third linear actuator 406 arranged between the second vertical track 234 and the second horizontal track 238, a fourth linear actuator 408 associated with the second horizontal track 238, a fifth linear actuator 410 arranged between the second horizontal track 238 and the first vertical track 232, and a sixth linear actuator 412 associated with the first vertical track 232. Herein, the first linear actuator 402, the second linear actuator 404, the third linear actuator 406, the fourth linear actuator 408, the fifth linear actuator 410 and the sixth linear actuator 412 together constitute the plurality of linear actuators 414 (as schematically represented in FIG. 4B), and move each one of the plurality of shoe storing shelves 104 along the path in the form of a loop defined sequentially along the first horizontal track 236, the second vertical track 234, the second horizontal track 238 and the first vertical track 232. The shoe organizer unit 100 further includes a first support actuator 416 and a second support actuator 418. Each of the first support actuator 416 and the second support actuator 418 may support one or more of the shoe storing shelves 104 at one or more stages during their movement along the path. For instance, the first support actuator 416 may support the shoe storing shelf 104 by engaging with the first projection 332 located on the left side wall 308A when the shoe storing shelf 104 may be located at an upper end of the second vertical track 234, and the second support actuator 418 may support the shoe storing shelf 104 by engaging with the second projection 334 located on the right side wall 308B when the shoe storing shelf 104 may be located at an upper end of the first vertical track 232. In the present examples, the first support actuator 416 and the second support actuator 418 may also be linear actuators without any limitations.

As used herein, the term "linear actuator" refers to an electric, hydraulic, electro-hydraulic, pneumatic, or mechanical device that generates force which is directed in a straight line. One common example of a "linear actuator" is a double-acting hydraulic actuator which includes a cylinder, a piston within the cylinder, and a rod attached to the piston. By increasing the pressure within the cylinder on one side of the piston (over that on the opposite side of the piston), the rod will extend from the cylinder or retract into the cylinder. Other types of linear actuators may be contemplated without any limitations. In an aspect, the linear actuators 414 may be in the form of servo motors (like 2 Amp, 200 Watt, 240 Volts servo motors as widely available) coupled with gears and other mechanical arrangements to enable precise control of movement of the shoe storing shelves 104 in the cabinet 102, e.g., to allow for a particular shoe storing shelf 104 to be positioned at a particular location (like, a shoe reception area as discussed later). The linear actuators 414 are schematically represented in FIG. 4A, and it may be appreciated that the depicted positions of the linear actuators 414, the first support actuator 416 and the second support actuator 418 in FIG. 4A are exemplary only for purposes of explanation and shall not be construed as limiting to the present disclosure.

Further, the shoe organizer unit 100 includes a plurality of position sensors. Each position sensor is operatively connected to a linear actuator (i.e., one of the plurality of linear actuators 414). In particular, the shoe organizer unit 100 includes a first position sensor 422 operatively connected to the first linear actuator 402 (and thereby the first horizontal track 236), a second position sensor 424 operatively connected to the second linear actuator 404 (and thereby the second vertical track 234), a third position sensor 426 operatively connected to the fourth linear actuator 408 (and thereby the second horizontal track 238) and a fourth position sensor 428 operatively connected to the sixth linear actuator 412 (and thereby the first vertical track 232). Herein, the first position sensor 422, the second position sensor 424, the third position sensor 426 and the fourth position sensor 428 together constitute the plurality of position sensors 420 (as schematically represented in FIG. 4B). Each position sensor 422, 424, 426, 428 is configured to generate a position signal in response to sensing a presence of the shoe storing shelf 104 near its respective linear actuator 402, 404, 408, 412. In the present examples, the plurality of position sensors 420 may be in the form of motion sensors, proximity sensors or the like, as known in the art. Herein, the term "position sensor" shall be understood to mean or describe a sensor that measures or estimates position and/or any time-based derivative of position, such as velocity and/or acceleration. The position sensors 420 are schematically represented in FIG. 4A, and it may be appreciated that the depicted positions of the position sensors 420 in FIG. 4A are exemplary only for purposes of explanation and shall not be construed as limiting to the present disclosure.

In an aspect of the present disclosure, the shoe organizer unit 100 includes a shoe reception area 430 (sometimes referred to as "shelf reception area 430") of the cabinet 102. Herein, the shoe reception area 430 is located at a base (generally referenced by the numeral 432 in FIG. 4A) in the cabinet 102. Specifically, the shoe reception area 430 is located at the base 432 of the second column 228, in the cabinet 102. Herein, the base 432 is generally complementary to the cabinet bottom 206, and corresponds to the second column 228 in the cabinet 102. As discussed in reference to FIGS. 2A to 2D, the central divider 220 is positioned with the gap from the cabinet bottom 206. The shoe reception area 430 of FIG. 4A, in the second column 228 of the cabinet 102, may be located at a same gap from the base 432. In other words, a height of the shoe reception area 430 from the base 432 in the second column 228 is about same as the gap between the central divider 220 and the cabinet bottom 206, in the cabinet 102. Further, the shoes may specifically be positioned in a shoe cavity in the shoe reception area 430, with the shoe cavity being a portion of the shoe reception area 430. In the present illustrations, the shoe cavity has not been explicitly shown and has been generally represented by the same numeral 430 as the shoe reception area 430.

The shoe organizer unit 100 further includes an ultraviolet lamp 434 (schematically represented in FIG. 4A) located on the base 432 of the second column 228. The ultraviolet lamp 434 may be any semiconductor radiation source, such as an ultraviolet ("UV") light emitting diode ("LED") device, that emits light at a short wavelength, e.g., near-violet or ultraviolet light. Such near-violet or ultraviolet light has disinfectant properties. The ultraviolet lamp 434 is positioned such that light generated by the ultraviolet lamp 434 shines into the shoe reception area 430. Therefore, when the shoes are received in one of the shoe storing shelf 104 positioned in the shoe reception area 430, those shoes get sterilized (disinfected) by the ultraviolet light provided by the ultraviolet lamp 434. The shoe organizer unit 100 further includes a proximity sensor 436 (schematically represented in FIG. 4A) located in the shoe reception area 430. The proximity sensor 436 is configured to detect the shoe storing shelf 104, when the shoe storing shelf 104 is positioned in the shoe reception area 430. The proximity sensor 436 may be any suitable sensor, including a motion sensor as known in the art. The shoe organizer unit 100 further includes a power source 438 (schematically represented in FIG. 4A) located within the central divider 220, of the cabinet 102. The term power source 438, as used herein, may include a renewable power source, a non-renewable power source, a generator, an AC/DC power supply, and the like, without any limitations. The shoe organizer unit 100 further includes a switch 440 (shown in FIG. 4B) operatively connected to the proximity sensor 436 and the ultraviolet lamp 434. The switch 440 is configured to provide power from the power source 438 to the ultraviolet lamp 434 when the proximity sensor 436 detects the shoe storing shelf 104 in the shoe reception area 430. Herein, the switch 440 may be an electromechanical switch, sometimes called electronics switch, which is widely used to make, break, or change the routing of electrical and electronic current flow in circuits; e.g., in the present circuit, from the power source 438 to the ultraviolet lamp 434. It is to be understood that the term "switch" as used herein is meant to broadly encompass any device capable of performing a switching function, and is not restricted to any particular kind of switch described herein. In some examples, the shoe organizer unit 100 further includes a timer 442 (shown in FIG. 4B) connected to the switch 440. In case of the switch 440 being electromechanical switch, the timer 442 may be an electromechanical cam timer which uses a small synchronous AC motor for turning a cam against switch contacts to regulate the switch 440. The timer 442 is configured to turn off the switch 440 after a predetermined time period. Herein, the predetermined time period may be defined as a sufficient time period for completing disinfection of the shoe(s) in the shoe storing shelf 104 positioned in the shoe reception area 430 by the ultraviolet light provided by the ultraviolet lamp 434.

In an aspect of the present disclosure, the shoe organizer unit 100 includes an actuator switch 452. In the present examples, the actuator switch 452 may be in the form of a button that may be pressed by the user of the shoe organizer unit 100. The actuator switch 452 is located on the front surface 230 of the central divider 220 at a location in a range of six inches to three feet above the cabinet bottom 206. Such location of the actuator switch 452 may provide suitable height to allow the user to comfortably reach and press the actuator switch 452, as and when required. In an example, when the actuator switch 452 is located at lower end of the range of six inches to three feet above the cabinet bottom 206, the actuator switch 452 may be pressed by the user using his/her foot; on the other hand, when the actuator switch 452 is located at upper end of the range of six inches to three feet above the cabinet bottom 206, the actuator switch 452 may be pressed by the user using his/her hand. The actuator switch 452 is configured to generate an actuator switch signal when pressed. Herein, the plurality of linear actuators 414 is configured to move each shoe storing shelf 104 along the path from a current position on the path to a next position along the path upon receiving the actuator switch signal. That is, when the actuator switch 452 is pressed and subsequently the actuator switch signal is generated, the plurality of linear actuators 414 are activated to work in conjunction to cause the shoe storing shelves 104 to move along the path defined sequentially along the first horizontal track 236, the second vertical track 234, the second horizontal track 238 and the first vertical track 232.

In an aspect of the present disclosure, the shoe organizer unit 100 includes a controller 460 located in the central divider 220. In the present examples, the controller 460 may be located inside the extrusion 231 defined in the central divider 220, or may be located on the front surface 230 of the central divider 220. Herein, the controller 460 may be any processing device, system, or part thereof that controls at least one operation of the device. The controller 460 may be implemented in hardware, firmware or software, or some combination of at least two of the same. The controller 460 may be associated with a memory 462. The controller 460 may be powered by the power source 438 as described in the preceding paragraphs. The controller 460 is operatively connected to receive the position signal from each position sensor 422, 424, 426, 428 and the actuator switch signal from the actuator switch 452. In the present examples, the controller 460 may be connected to the plurality of position sensors 420 and the actuator switch 452 in a wired or a wireless manner, without any limitations. The controller 460 includes circuitry and a processor having program instructions (as will be described later in the description) configured to provide power to each of the plurality of linear actuators 414 to move a respective shoe storing shelf 104 along the path upon receiving the actuator switch signal from the actuator switch 452. Specifically, when a particular shoe storing shelf 104 is detected by any one of the plurality of position sensors 420, and the operational requirement of the shoe organizer unit 100 needs that the said particular shoe storing shelf 104 be moved, then the controller 460 may provide power (say, from the power source 438) to each of the plurality of linear actuators 414 to allow for movement of the said particular shoe storing shelf 104, along with the other shoe storing shelves 104, along the path. In an example, when it may be detected that the shoes are now received in a particular shoe storing shelf 104 located in the shoe reception area 430 on the second vertical track 234, and if the corresponding second position sensor 424 detects that the said particular shoe storing shelf 104 is still located in the shoe reception area 430, the controller 460 may provide power to the plurality of linear actuators 414 to move the said particular shoe storing shelf 104 upwards and bring another shoe storing shelf 104 from bottom of the first column 226 of the cabinet 102 to the shoe reception area 430 therein.

In an aspect of the present disclosure, the shoe organizer unit 100 includes a first transparent viewing window 472 covering a first front surface (not shown) of the first column 226. The first front surface refers to a plane extending between the first front surface 216 of the first side wall 208 and the front surface 230 of the central divider 220 of the cabinet 102. The first transparent viewing window 472 may be in the form of a glass pane or the like, which may be supported over the first side wall 208 and the central divider 220 of the cabinet 102. In an example, the first transparent viewing window 472 may be supported over the first side wall 208 and the central divider 220 by fasteners, such as nuts and bolts, or the like. In another example, the first transparent viewing window 472 may be supported over the first side wall 208 by a hinge mechanism to allow for opening the first transparent viewing window 472 with respect to the cabinet 102 and accessing inside thereof. In the present examples, the first transparent viewing window 472 may extend from the cabinet top 204 to the cabinet bottom 206 in the cabinet 102. Further, the shoe organizer unit 100 includes a second transparent viewing window 474 covering a first portion of a second front surface (not shown) of the second column 228. Similar to the first front surface, the second front surface refers to a plane extending between the second front surface 218 of the second side wall 210 and the front surface 230 of the central divider 220 of the cabinet 102, generally in the same plane as the first front surface. The second transparent viewing window 474 may also be in the form of a glass pane or the like, which may be supported over the second side wall 210 and the central divider 220 of the cabinet 102. In an example, the second transparent viewing window 474 may be supported over the second side wall 210 and the central divider 220 by fasteners, such as nuts and bolts, or the like. In another example, the second transparent viewing window 474 may be supported over the second side wall 210 by a hinge mechanism to allow for opening the second transparent viewing window 474 with respect to the cabinet 102 and accessing inside thereof. Further, a second portion of the second front surface of the second column 228 has an open area. Herein, the open area corresponds to the shoe reception area 430 (as described above), and the two terms have been interchangeably used hereinafter. It may be appreciated that the first portion of the second front surface corresponds to portion of the second column 228 other than the open area 430 therein. That is, the second transparent viewing window 474 may extend from the cabinet top 204 to a height just above the open area 430 in the cabinet 102. The open area 430 extends from the cabinet bottom 206 to two feet above the cabinet bottom 206. The open area 430 is configured to provide access to the shoe storing shelf 104 located in the second column 228 on the cabinet bottom 206. Therefore, only the shoe storing shelf 104 located in the open area 430 may be accessed by the user for storing the shoes therein, and thus makes it convenient and fool-proof for the user to locate the shoe storing shelf 104 to be used for storing shoes in the shoe organizer unit 100. As will be understood, the transparent viewing windows 472, 474 provide secure storage of the shoes within the cabinet 102, for the shoe organizer unit 100.

In an aspect of the present disclosure, the shoe organizer unit 100 includes a first cross member 482 located at the cabinet top 204. The first cross member 482 may be in the form of a slab of wood or the like. The first cross member 482 may be disposed along the horizontal axis 'X' and supported between the first side wall 208 and the second side wall 210 of the cabinet 102. The shoe organizer unit 100 also includes a second cross member 484 located at a bottom of the second transparent viewing window 474. In other words, the second cross member 484 may be located right above the open area 430 in the cabinet 102. The second cross member 484 may also be in the form of a slab of wood or the like. The second cross member 484 may be disposed along the horizontal axis 'X' and supported between the central divider 220 and the second side wall 210 of the cabinet 102. The second cross member 484 may allow to support (accommodate) other components therein. The shoe organizer unit 100 further includes an ultraviolet lamp 486 (similar to the ultraviolet lamp 434) located on the second cross member 484 such that ultraviolet light projects into a shoe cavity (corresponding to the shoe reception area 430, with the two terms being interchangeably used hereinafter) when the ultraviolet lamp 486 is turned on. Herein, the ultraviolet lamp 486 is operatively connected to the controller 460. The shoe organizer unit 100 further includes a proximity sensor 488 (shown in FIG. 4B), which is same as the proximity sensor 338 located on one of the upper surface 312 of the left shoe retainer 314A and the right shoe retainer 314B (as shown in FIG. 3D). The proximity sensor 488 is configured to detect the insertion of the shoe in corresponding one or both of the left shoe retainer 314A and the right shoe retainer 314B. The proximity sensor 488 is also operatively connected to the controller 460. The controller 460 is configured to turn on the ultraviolet lamp 486 (by supplying power form the power source 438) when the proximity sensor 488 detects the insertion of the shoe in either the left shoe retainer 314A and the right shoe retainer 314B, and to turn off a switch (such as, the switch 440) after a predetermined time period. Herein, the predetermined time period may be defined as a sufficient time period for completing sterilization (disinfection) of the shoe(s) in corresponding one or both of the left shoe retainer 314A and the right shoe retainer 314B by the ultraviolet light provided by the ultraviolet lamp 486.

In an aspect of the present disclosure, the shoe organizer unit 100 includes a keypad 492. The keypad 492 is located on the central divider 220. The keypad 492 may be located directly below the actuator switch 452. In other examples, the keypad 492 may be located above the actuator switch 452 on the central divider 220 or any other location convenient to a user. Herein, the keypad 492 may be in the form of a keyboard, indicating the user input devices having lettered and/or numbered keys. The term "keypad" is understood to include other forms of data entry devices, the keys being presented by way of example. For instance, in other examples, the keypad may be in the form of a touch screen. In the present examples, the keypad 492 is associated with a display 494. The keypad 492 is configured to generate a shoe shelf identification code for each shoe storing shelf 104 located in the open area 430 and display the shoe shelf identification code on the display 494. The shoe shelf identification code is generated and displayed when a pair of shoes is inserted into one of the shoe storing shelves 104. The shoe shelf identification code may be unique to each of the shoe storing shelves 104, and thereby the pair of shoes stored therein. The keypad 492 is further configured to allow inputting of the shoe shelf identification code by the user of the shoe organizer unit 100, when the pair of shoes as stored corresponding to the shoe shelf identification code may need to be retrieved. In an aspect, the keypad 492 is associated with a printer 496 (schematically shown in FIG. 4A), located in the central divider 220 itself. In an example, the printer 496 may be integrated with the keypad 492. The printer is configured to print a shoe shelf identification code card with the shoe shelf identification code printed thereon, and dispense the shoe shelf identification code card. For this purpose, the printer 496 may receive the shoe shelf identification code from the controller 460. The keypad 492 also includes a card receiving slot 498 for inputting the shoe shelf identification code card by the user of the shoe organizer unit 100, when required to retrieve the stored pair of shoes corresponding to the printed shoe shelf identification code in the shoe shelf identification code card. The card receiving slot 498 may be configured to read the printed shoe shelf identification code on the shoe shelf identification code card received thereby, and transmit the shoe shelf identification code to the controller 460. The shoe organizer unit 100 also includes the memory 462 operatively connected to the controller 460. The memory 462 is configured to receive the shoe shelf identification code, from the controller 460. That is, when the shoe shelf identification code is generated by the controller 460, the generated shoe shelf identification code is stored in the memory 462. The keypad 492 is further configured to receive a shoe shelf identification code input and transmit the shoe shelf identification code input to the controller 460. It may be appreciated that the shoe shelf identification code input may be received from the user, by pressing of the keys on the keypad 492 by the user. The controller 460 is further configured to match the shoe shelf identification code input to the shoe shelf identification code stored in the memory 462. If the shoe shelf identification code input matches with the shoe shelf identification code, the controller 460 is configured to identify a particular shoe storing shelf 104 associated with the shoe shelf identification code. The controller 460 is further configured to provide power to the linear actuators 414 to move the particular shoe storing shelf 104 to the open area 430, so that the user is able to access the particular shoe storing shelf 104 for retrieving the stored shoes therefrom.

Figure 5:
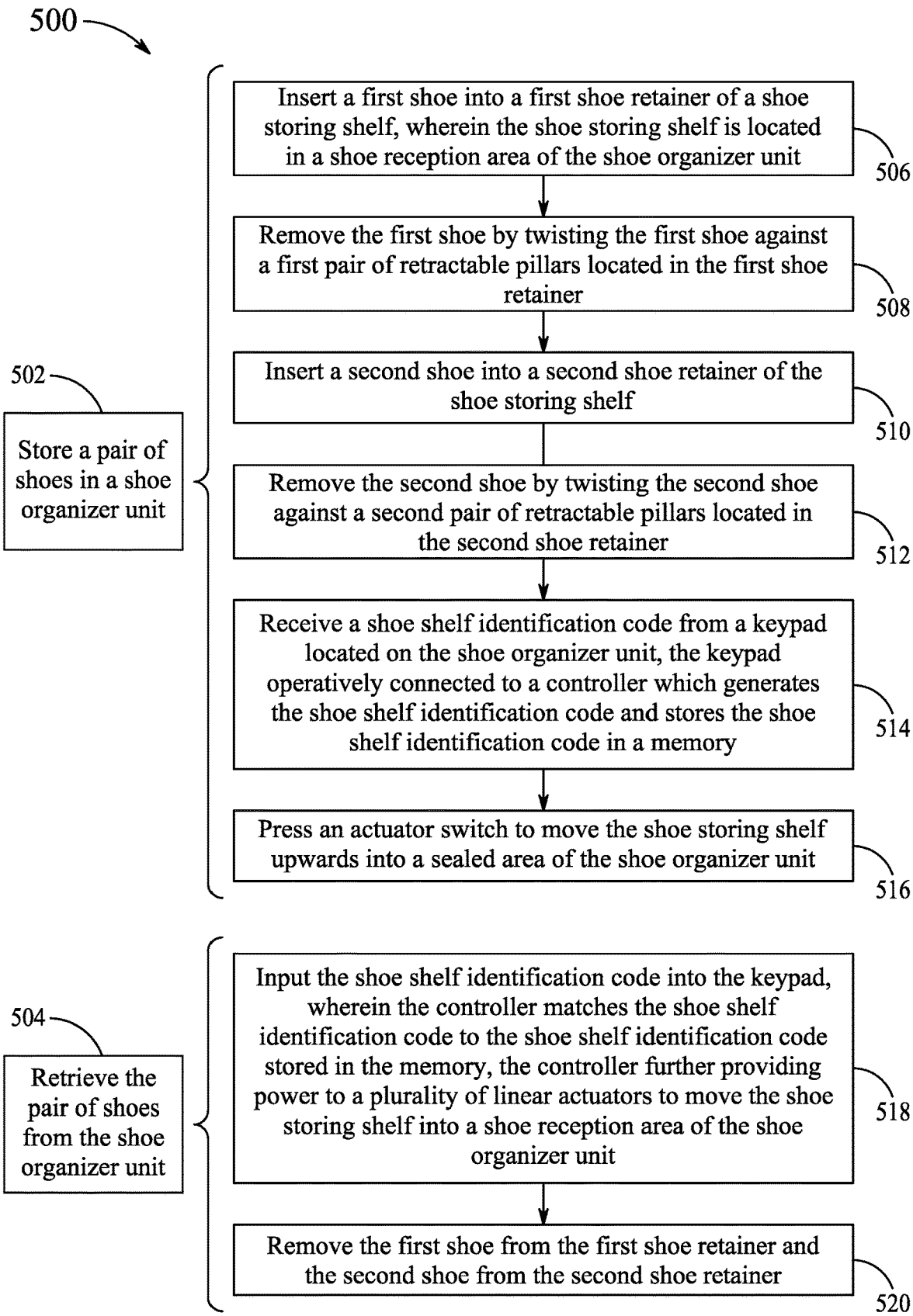
FIG. 5 is an exemplary flowchart of a method of using the shoe organizer unit, according to certain embodiments.

Referring to FIG. 5, an exemplary flowchart of a method 500 of using the shoe organizer unit 100 is illustrated. The method 500 is described with reference to the shoe organizer unit 100 illustrated in FIG. 1 through FIG. 4B. The method 500 is further described with reference to FIGS. 7A to 7E. The method 500 broadly involves two stages, a first stage 502 which involves storing a pair of shoes in the shoe organizer unit 100 and a second stage 504 which involves retrieving the pair of shoes from the shoe organizer unit 100. Each of the first stage 502 and the second stage 504 involve multiple steps as described in the proceeding paragraphs.

At step 506, the first stage 502 of the method 500 includes inserting a first shoe into the first shoe retainer 314A of the shoe storing shelf 104, wherein the shoe storing shelf 104 is located in the shoe reception area 430 of the shoe organizer unit 100. That is, as illustrated in FIG. 7A, the user may insert the first shoe into the first shoe retainer 314A of the shoe storing shelf 104, when the shoe storing shelf 104 is located in the shoe reception area 430 of the shoe organizer unit 100. As may be understood that when the shoe storing shelf 104 is located in the shoe reception area 430, the shoe storing shelf 104 is accessible to the user and thus the user could insert the first shoe therein. The first shoe is inserted between the first pair of retractable pillars 318A such that the retractable pillars 318A may retract and grip the first shoe.

At step 508, the first stage 502 of the method 500 includes removing the first shoe by twisting the first shoe against the first pair of retractable pillars 318A located in the first shoe retainer 314A. As illustrated in FIG. 7B and FIG. 7C, the first shoe may be gripped by the retractable pillars 318A in the first shoe retainer 314A. Particularly, as shown in FIG. 7C, when the first shoes are inserted, the elastic adjustable covering 320 compresses to cause the first pair of retractable pillars 318A to retract and thereby grip the first shoes. Therefore, the user may easily remove the first shoe from his/her foot by pulling the corresponding foot out from the first shoe to cause the first shoe to twist against the first pair of retractable pillars 318A and thereby enable removing of the first shoe from the foot of the user. This enables the user to remove the first shoe without him/her needing to bend or use his/her hand for shoe removing purposes.

In an aspect, the method 500 includes twisting the first shoe against the first pair of retractable pillars 318A while holding a handrail located on the front wall of the cabinet 102. Particularly, the first shoe may be twisted against the first pair of retractable pillars 318A while the user is holding the first hand rail 240 located on the first front surface 216 of the first side wall 208 of the cabinet 102. This provides support for the user while pulling the foot out of the first shoe, as one of the legs (which may be used to push the inserted shoe out from its back) may be suspended in air at that instant.

At step 510, the first stage 502 of the method 500 includes inserting a second shoe into a second shoe retainer of the shoe storing shelf. That is, as illustrated in FIG. 7A, the user may insert the second shoe into the second shoe retainer 314B of the shoe storing shelf 104, when the shoe storing shelf 104 is located in the shoe reception area 430 of the shoe organizer unit 100. As may be understood that when the shoe storing shelf 104 is located in the shoe reception area 430, the shoe storing shelf 104 is accessible to the user and thus the user could insert the second shoe therein. The second shoe is inserted between the second pair of retractable pillars 318B such that the retractable pillars 318B may retract and grip the second shoe.

At step 512, the first stage 502 of the method 500 includes removing the second shoe by twisting the second shoe against the second pair of retractable pillars 318B located in the second shoe retainer 314B. As illustrated in FIG. 7B and FIG. 7C, the second shoe may be gripped by the retractable pillars 318B in the second shoe retainer 314B. Particularly, as shown in FIG. 7C, when the second shoes are inserted, the elastic adjustable covering 320 compresses to cause the second pair of retractable pillars 318B to retract and thereby grip the second shoes. Therefore, the user may easily remove the second shoe from his/her foot by pulling the corresponding foot out from the second shoe to cause the second shoe to twist against the second pair of retractable pillars 318B and thereby enable removing of the second shoe from the foot of the user. This enables the user to remove the second shoe without him/her needing to bend or use his/her hand for shoe removing purposes.

In an aspect, the method 500 includes twisting the second shoe against the second pair of retractable pillars 318B while holding a handrail located on the front wall of the cabinet 102. Particularly, the second shoe may be twisted against the second pair of retractable pillars 318B while the user is holding the second hand rail 242 located on the second front surface 218 of the second side wall 210 of the cabinet 102. This provides support for the user while pulling the foot out of the second shoe, as one of the legs may be suspended in air at that instant.

At step 514, the first stage 502 of the method 500 includes receiving the shoe shelf identification code from the keypad 492 located on the shoe organizer unit 100. The keypad 492 is operatively connected to the controller 460 which generates the shoe shelf identification code and stores the shoe shelf identification code in the memory 462. The shoe shelf identification code is unique and assigned to a particular shoe storing shelf 104 been used by the user for storage of the shoes thereof.

In an aspect, the first stage 502 of the method 500 includes receiving a shoe shelf identification code card from the printer 496 located on the keypad 492 when storing the pair of shoes in the shoe organizer unit 100. That is, when the shoe shelf identification code is generated, a physical copy of the shoe shelf identification code card is dispensed by the printer 496 with the shoe shelf identification code printed thereon for reference of and perusal by the user.

At step 516, the first stage 502 of the method 500 includes pressing the actuator switch 452 to move the shoe storing shelf 104 upwards into a sealed area of the shoe organizer unit 100. Herein, the "sealed area" is complementary to the first portion of the second front surface, which corresponds to portion of the second column 228 other than the open area 430 therein. When the actuator switch 452 is pressed, the controller 460 receives the actuator switch signal and in turn provide power to each of the plurality of linear actuators 414 to move the shoe storing shelf 104 been used upward into the sealed area to efficiently store the shoes in the shoe organizer unit 100, and further so as not to be accessible without the shoe shelf identification code and thereby prevent possible theft of the shoes stored therein.

At step 518, the second stage 504 of the method 500 includes inputting the shoe shelf identification code into the keypad 492. Herein, the controller matches the shoe shelf identification code to the shoe shelf identification code stored in the memory 462. The controller 460 further provides power to the plurality of linear actuators 414 to move the shoe storing shelf 104 into the shoe reception area 430 of the shoe organizer unit 100. That is, when the user inputs the shoe shelf identification code, the controller matches the inputted shoe shelf identification code to the shoe shelf identification code stored in the memory 462, and if it matches, the controller 460 moves the shoe storing shelf 104 corresponding to the inputted shoe shelf identification code into the shoe reception area 430 of the shoe organizer unit 100, so as to allow the user to retrieve his/her shoes therefrom.

In an aspect, the method 500 includes inputting the shoe shelf identification code card into the card receiving slot 498 in the keypad 492 when retrieving the pair of shoes from the shoe organizer unit 100. That is, instead of manually entering the shoe shelf identification code via the keypad 492 or the like, the user may simply input the dispensed (issued) shoe shelf identification code card into the card receiving slot 498. The controller 460 may read the shoe shelf identification code from the inputted shoe shelf identification code card itself.

At step 520, the second stage 504 of the method 500 includes removing the first shoe from the first shoe retainer 314A and the second shoe from the second shoe retainer 314B. That is, when the shoe storing shelf 104 is positioned in the shoe reception area 430 of the shoe organizer unit 100, the user may remove the stored shoes therefrom.

Figure 6:
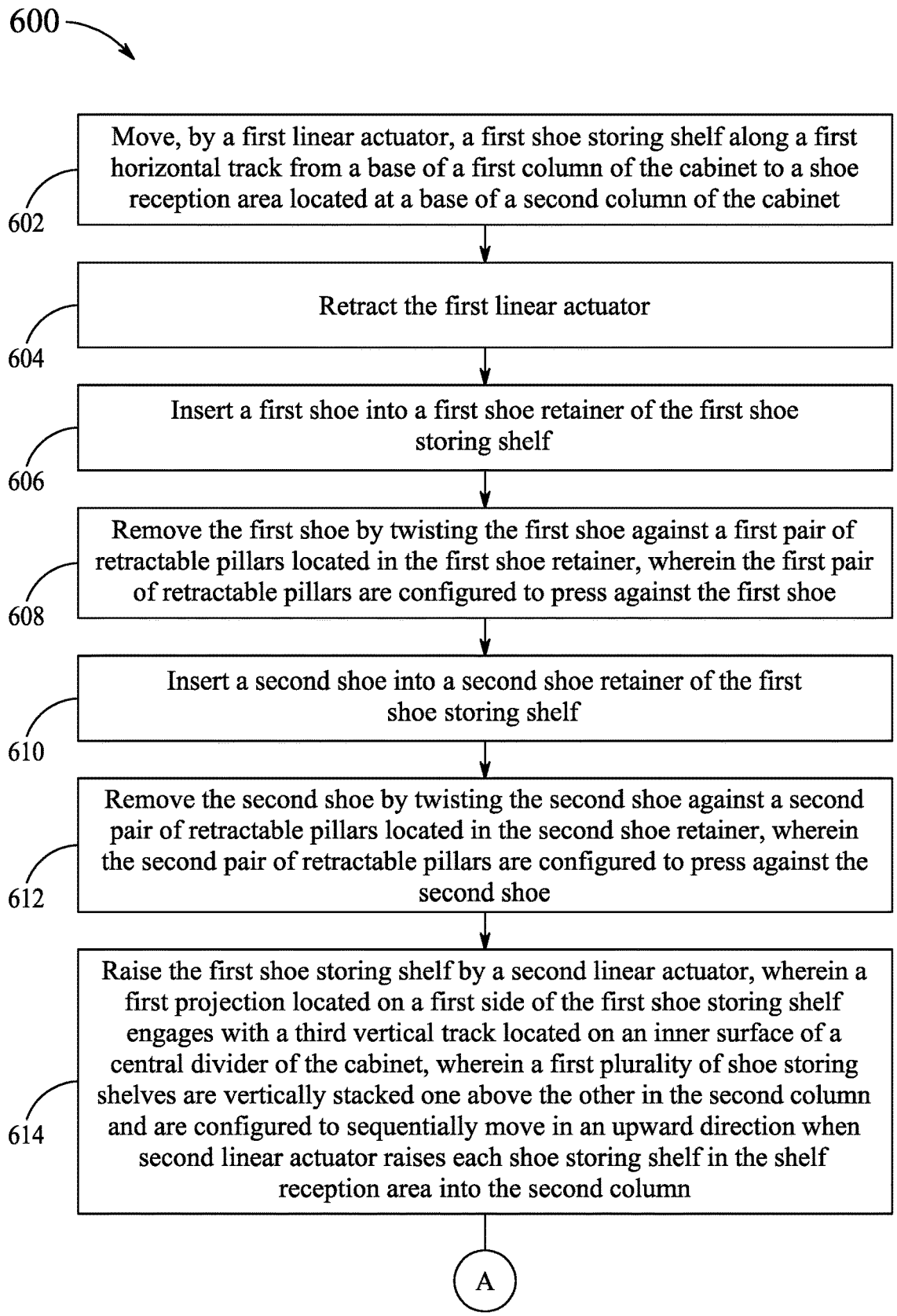
FIG. 6 is an exemplary flowchart of a method for storing shoes in a plurality of shoe storing shelves of the shoe organizer unit, according to certain embodiments.
Figure 6:
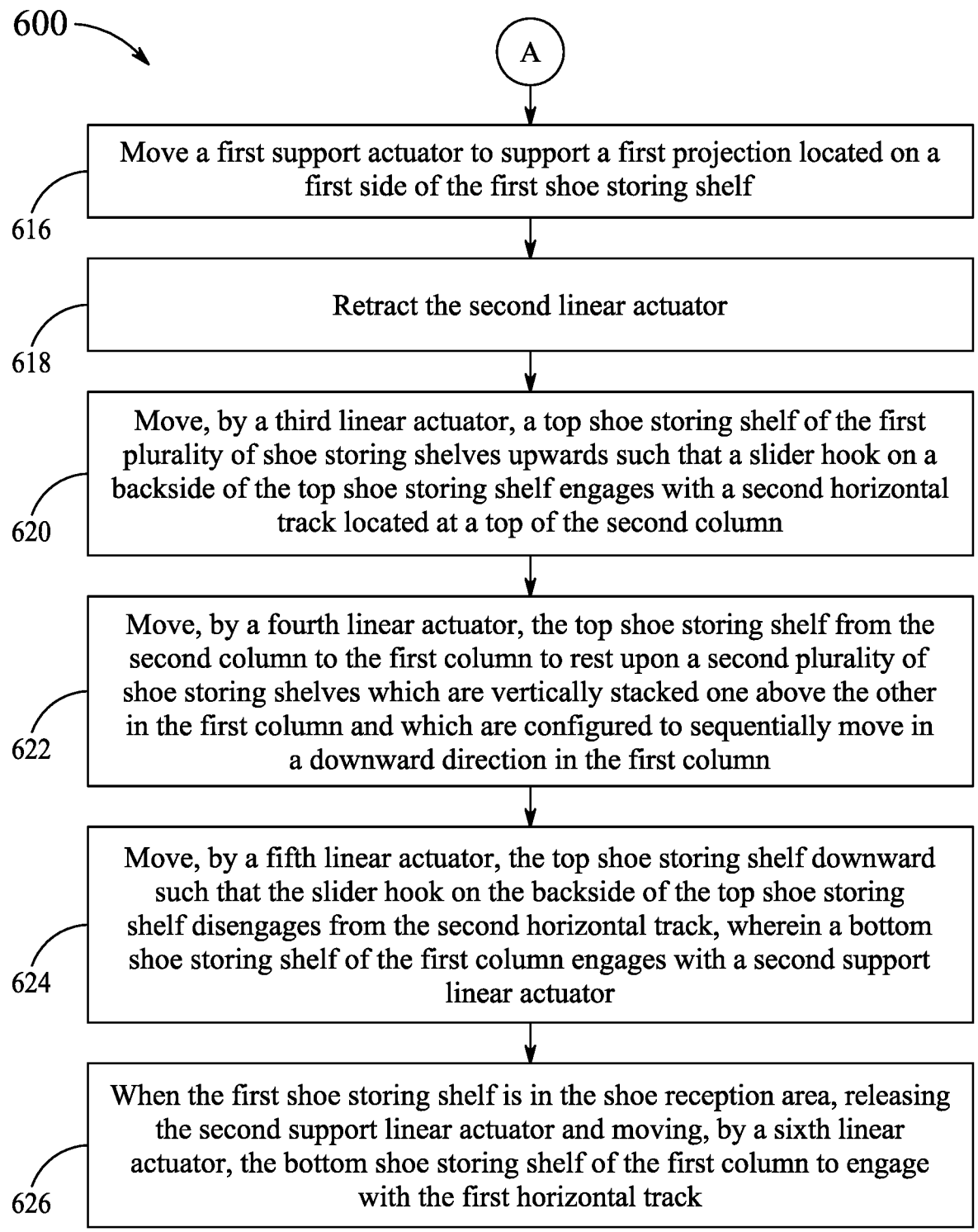

Referring to FIG. 6, an exemplary flowchart of a method 600 for storing shoes in the plurality of shoe storing shelves 104 of the shoe organizer unit 100, with the shoe organizer unit 100 including the cabinet 102, is illustrated. The method 600 is described with reference to the shoe organizer unit 100 illustrated in FIG. 1 through FIG. 4B. The method 600 is further described with reference to FIGS. 7A-7E.

Figure 7D:
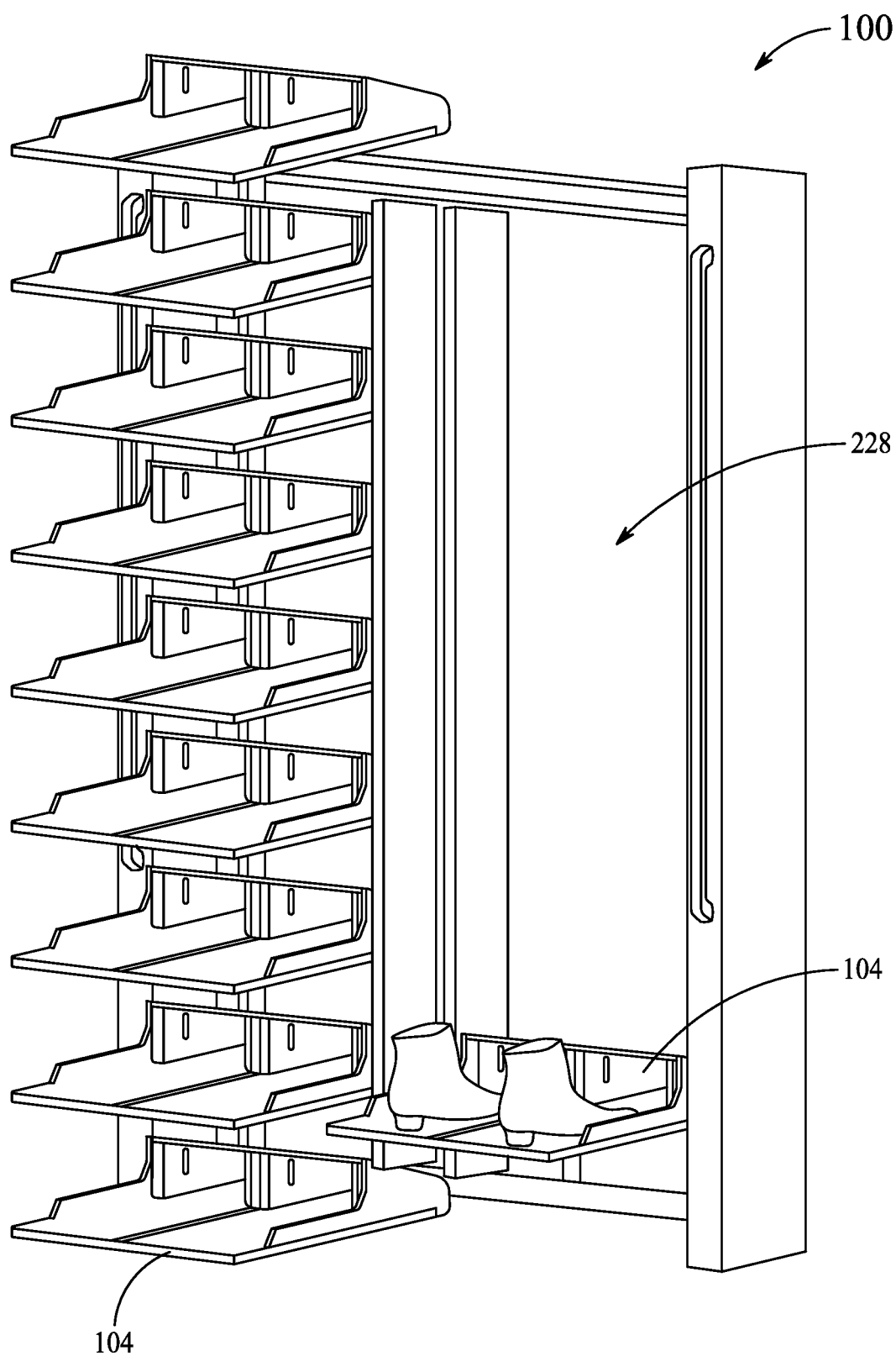
FIG. 7D is a diagrammatic illustration of a step involved in using the shoe organizer unit of FIG. 1, according to certain embodiments.
Figure 7E:
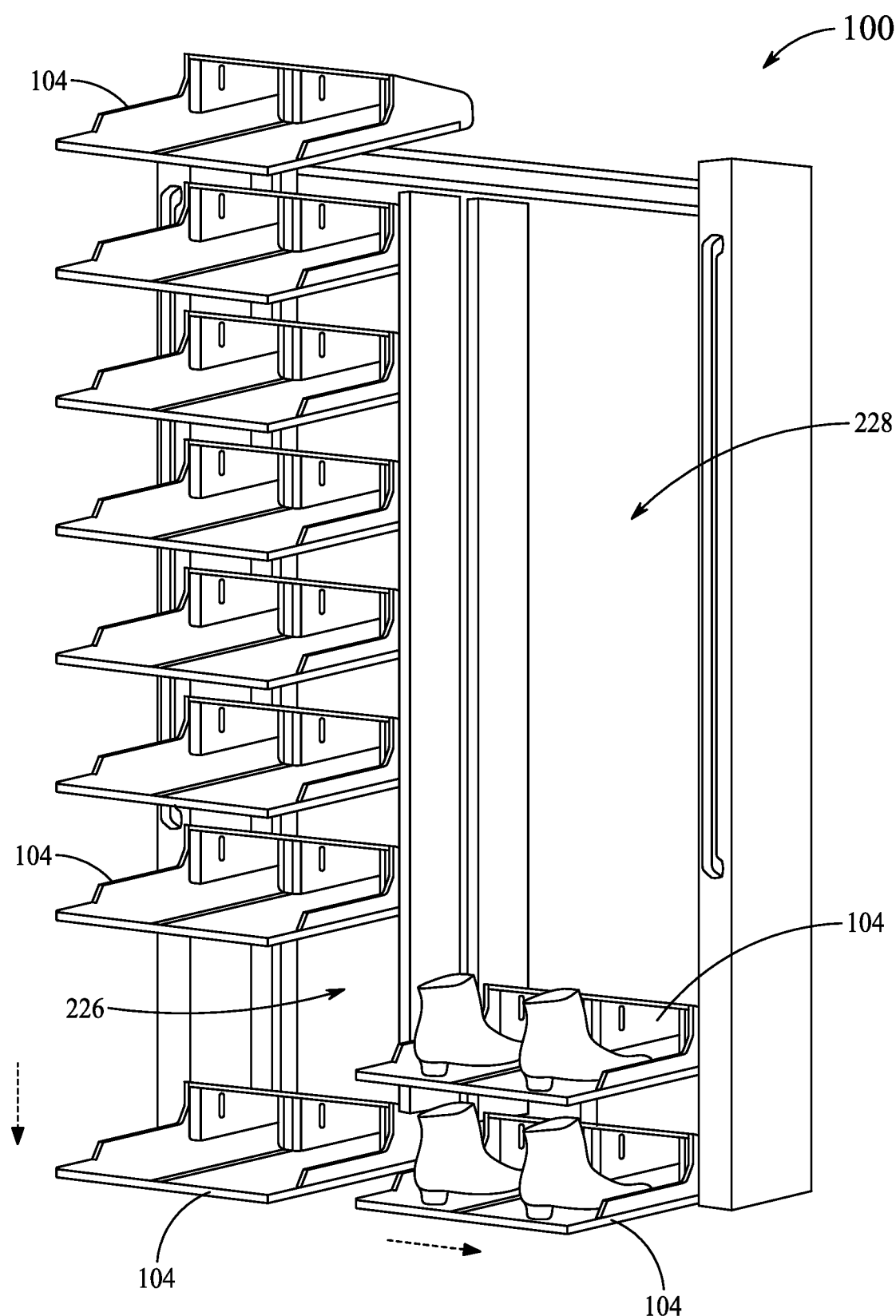
FIG. 7E is a diagrammatic illustration of a step involved in using the shoe organizer unit of FIG. 1, according to certain embodiments.
Figure 7F:
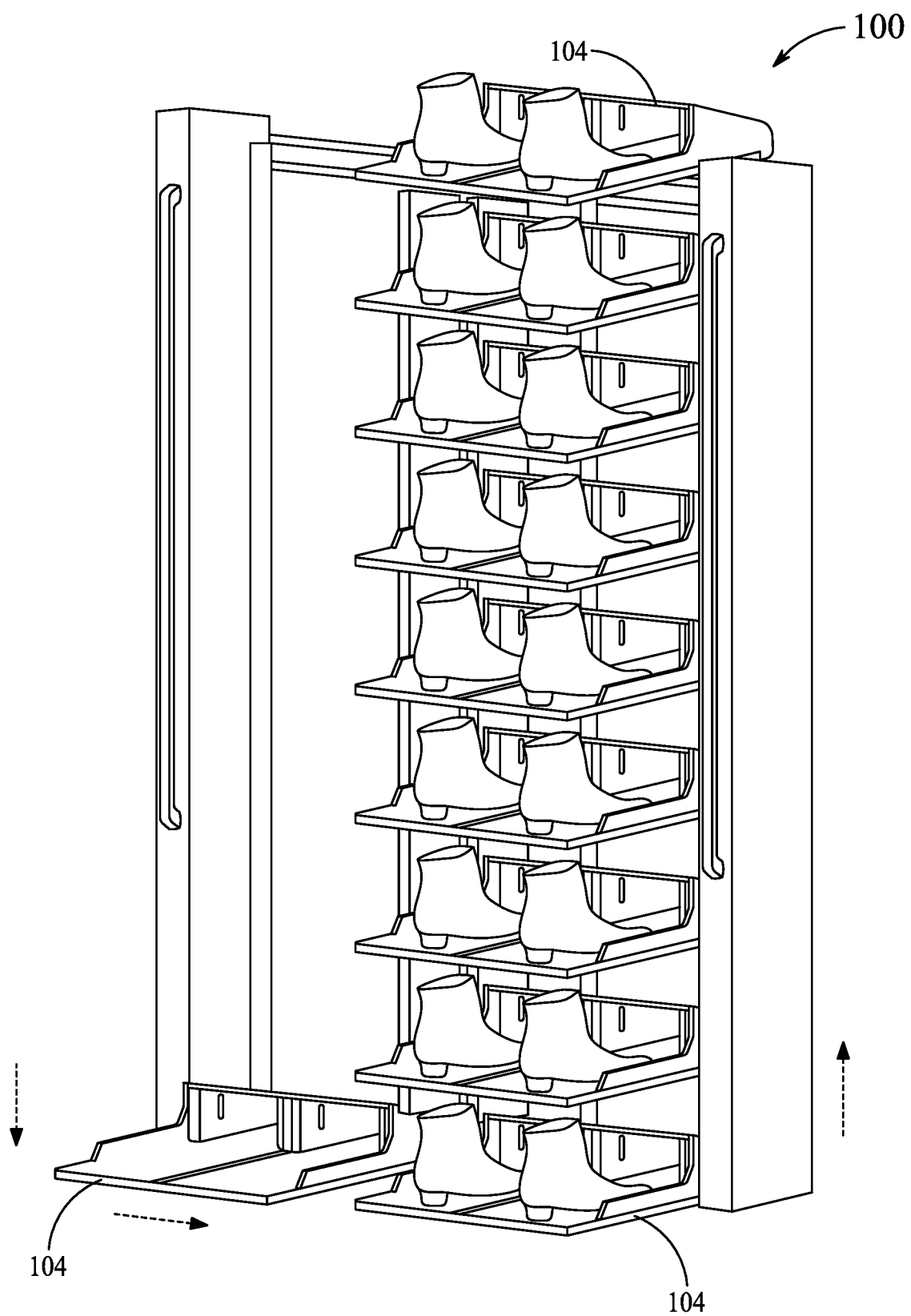
FIG. 7F is a diagrammatic illustration of a step involved in using the shoe organizer unit of FIG. 1, according to certain embodiments.

At step 602, the method 600 includes moving, by the first linear actuator 402, the first shoe storing shelf 104 along the first horizontal track 236 from a base 432 of the first column 226 of the cabinet 102 to the shoe reception area 430 located at the base 432 of the second column 228 of the cabinet 102. Herein, the first shoe storing shelf 104 may represent the lowermost shoe storing shelf 104 in the first column 226. The first shoe storing shelf 104 may be engaged with the first horizontal track 236 via the slider hook 336, when located at the base 432 of the second column 228. As illustrated in FIG. 7E and FIG. 7F, when the first linear actuator 402 is powered, the first shoe storing shelf 104 moves from the base 432 of the first column 226 to the shoe reception area 430 located at the base 432 of the second column 228 of the cabinet 102.

At step 604, the method 600 includes retracting the first linear actuator 402. That is, when the first shoe storing shelf 104 is moved to the shoe reception area 430 located at the base 432 of the second column 228 of the cabinet 102, the first linear actuator 402 is retracted so that the slider hook 336 is disengaged from the first horizontal track 236 of the first shoe storing shelf 104. Generally, simultaneously, the controller 460 powers the second linear actuator 404 to engage the first shoe storing shelf 104 with the second vertical track 234 via the second projection 334 thereof, so as to support the first shoe storing shelf 104 in the cabinet 102.

At step 606, the method 600 includes inserting the first shoe into the first shoe retainer 314A of the first shoe storing shelf 104. That is, as illustrated in FIG. 7A, the user may insert the first shoe into the first shoe retainer 314A of the shoe storing shelf 104, when the shoe storing shelf 104 is located in the shoe reception area 430 of the shoe organizer unit 100. As may be understood that when the shoe storing shelf 104 is located in the shoe reception area 430, the shoe storing shelf 104 is accessible to the user and thus the user could insert the first shoe therein. The first shoe is inserted between the first pair of retractable pillars 318A such that the retractable pillars 318A may retract and grip the first shoe.

At step 608, the method 600 includes removing the first shoe by twisting the first shoe against the first pair of retractable pillars 318A located in the first shoe retainer 314A. Herein, the first pair of retractable pillars 318A are configured to press against the first shoe. As illustrated in FIG. 7B and FIG. 7C, the first shoe may be gripped by the retractable pillars 318A in the first shoe retainer 314A, the user may easily remove the first shoe from his/her foot by pulling the corresponding foot out from the first shoe to cause the first shoe to twist against the first pair of retractable pillars 318A and thereby enable removing of the first shoe from the foot of the user. This enables the user to remove the first shoe without him/her needing to bend or use his/her hand for shoe removing purposes.

At step 610, the method 600 includes inserting the second shoe into the second shoe retainer 314B of the first shoe storing shelf 104. That is, as illustrated in FIG. 7A, the user may insert the second shoe into the second shoe retainer 314B of the shoe storing shelf 104, when the shoe storing shelf 104 is located in the shoe reception area 430 of the shoe organizer unit 100. As may be understood that when the shoe storing shelf 104 is located in the shoe reception area 430, the shoe storing shelf 104 is accessible to the user and thus the user could insert the second shoe therein. The second shoe is inserted between the second pair of retractable pillars 318B such that the retractable pillars 318B may retract and grip the second shoe.

At step 612, the method 600 includes removing the second shoe by twisting the second shoe against the second pair of retractable pillars 318B located in the second shoe retainer 314B. Herein, the second pair of retractable pillars 318B are configured to press against the second shoe. As illustrated in FIG. 7B and FIG. 7C, the second shoe may be gripped by the retractable pillars 318B in the second shoe retainer 314B, the user may easily remove the second shoe from his/her foot by pulling the corresponding foot out from the second shoe to cause the second shoe to twist against the second pair of retractable pillars 318B and thereby enable removing of the second shoe from the foot of the user. This enables the user to remove the second shoe without him/her needing to bend or use his/her hand for shoe removing purposes.

At step 614, the method 600 includes raising the first shoe storing shelf 104 by the second linear actuator 404. Herein, the first projection 332 located on the first side 308A of the first shoe storing shelf 104 engages with the fourth vertical track 235 located on an inner surface (i.e., the second inner surface 224) of the central divider 220 of the cabinet 102. Further, herein, the second projection 334 located on the second side 308B of the first shoe storing shelf 104 engages with the second vertical track 234 located on the second inner surface 214 of the second side wall 210 of the cabinet 102. As illustrated in FIG. 7D, the second linear actuator 404 may move the first shoe storing shelf 104 upward along the second vertical track 234 and the fourth vertical track 235.

Herein, a first plurality of shoe storing shelves are vertically stacked one above the other in the second column 228 and are configured to sequentially move in an upward direction when the second linear actuator 404 raises each shoe storing shelf 104 in the shelf reception area 430 into the second column 228. That is, as illustrated in FIG. 7F, when the second linear actuator 404 moves the first shoe storing shelf 104 positioned in the shelf reception area 430 upwards (along the vertical axis 'X') in the second column 228, other shoe storing shelves 104 that are vertically stacked one above the other in the second column 228 also sequentially move in the upward direction in the second column 228.

At step 616, the method 600 includes moving the first support actuator 416 to support the first projection 332 located on the first side 308A of the first shoe storing shelf 104. That is, when the first shoe storing shelf 104 has moved upward along the second column 228 at an end of the second vertical track 234, the controller 460 powers the first support actuator 416 to support the first shoe storing shelf 104 by engaging with the first projection 332 located on the first side 308A of the first shoe storing shelf 104.

At step 618, the method 600 includes retracting the second linear actuator 404. Since, the first shoe storing shelf 104 is supported by the first support actuator 416, this allows for the controller 460 to retract the second linear actuator 404, while keeping the first shoe storing shelf 104 in the second column 228 of the cabinet 102. The second linear actuator 404 is retracted to allow for the first shoe storing shelf 104 to be engaged with further elements along the path to be travelled thereby in the cabinet 102.

At step 620, the method 600 includes moving, by the third linear actuator 406, a top shoe storing shelf of the first plurality of shoe storing shelves 104 upwards such that the slider hook 336 on the backside 310 of the top shoe storing shelf engages with the second horizontal track 238 located at a top of the second column 228. Herein, as illustrated in FIG. 7F, the first shoe storing shelf 104 which may be at the top of the second column 228 (i.e., the end of the second vertical track 234) may be pushed upwards such that the slider hook 336 of the first shoe storing shelf 104 engages with the second horizontal track 238. In the process, the first support actuator 416 supporting the first shoe storing shelf 104 is disengaged therefrom.

At step 622, the method 600 includes moving, by the fourth linear actuator 408, the top shoe storing shelf 104 from the second column 228 to the first column 226 to rest upon a second plurality of shoe storing shelves which are vertically stacked one above the other in the first column 226 and which are configured to sequentially move in a downward direction in the first column 226. That is, when the first shoe storing shelf 104 is engaged with the second horizontal track 238, the controller 460 powers the fourth linear actuator 408 to move the top shoe storing shelf 104 along the horizontal axis 'X' from the second column 228 to the first column 226. At the first column 226, the top shoe storing shelf 104 is positioned above the other shoe storing shelves 104.

At step 624, the method 600 includes moving, by the fifth linear actuator 410, the top shoe storing shelf 104 downward such that the slider hook 336 on the backside 310 of the top shoe storing shelf 104 disengages from the second horizontal track 238. Herein, as illustrated in FIG. 7E, the top shoe storing shelf 104 which is at the top of the first column 226 may be pushed downwards such that the slider hook 336 of the shoe storing shelf 104 disengages from the second horizontal track 238 and move downward to an end of the first vertical track 232 in the first column 226. In the process, the shoe storing shelf 104 engages with the first vertical track 232.

Herein, a bottom shoe storing shelf 104 of the first column 226 engages with the second support actuator 418. For this purpose, the controller 460 moves the second support actuator 418 to support the second projection 334 located on the second side 308B of the bottom shoe storing shelf 104. That is, when the first shoe storing shelf 104 has moved downward along the first column 226 at an end of the first vertical track 232, the controller 460 powers the second support actuator 418 to support the bottom shoe storing shelf 104 by engaging with the second projection 334 located on the second side 308B of the bottom shoe storing shelf 104.

At step 626, the method 600 includes, when the first shoe storing shelf 104 is in the shoe reception area 430, releasing the second support actuator 418 and moving, by the sixth linear actuator 412, the bottom shoe storing shelf 104 of the first column 226 to engage with the first horizontal track 236. That is, once the bottom shoe storing shelf 104 of the first column 226 is disengaged from the second support actuator 418, the slider hook 336 of the bottom shoe storing shelf 104 of the first column 226 engages with the first horizontal track 236, and the sixth linear actuator 412 moves the bottom shoe storing shelf 104 along the first horizontal track 236 from the base 432 of the first column 226 back to the shoe reception area 430 in the base 432 of the second column 228.

In an aspect of the present disclosure, the method 600 further includes generating the actuation switch signal by the actuator switch 452 located on the front surface 230 of the central divider 220 at a location in a range of six inches to three feet above the cabinet bottom 206. That is, when the user has stored the shoes in the shoe storing shelf 104 positioned in the shoe reception area 430, the user may press the actuator switch 452 to generate the actuation switch signal. The method 600 further includes generating the position signal at each linear actuator 402, 404, 408, 412, by the plurality of position sensors 420, in response to sensing a presence of the shoe storing shelf 104 near its respective linear actuator 402, 404, 408, 412. That is, when the shoe storing shelf 104 is detected by any one of the position sensors 422, 424, 426, 428, the corresponding position sensor 422, 424, 426, 428 generates the position signal to indicate the presence of the shoe storing shelf 104. The method 600 further includes receiving, by the controller 460 located in the central divider 220 between the first column 226 and the second column 228, the position signal from each position sensor 422, 424, 426, 428 and the actuator switch signal (from the actuator switch 452). The controller 460 including circuitry and a processor having program instructions configured to provide power to each of the linear actuators 414 to move the respective shoe storing shelf 104 along upon receiving the actuator switch signal. That is, when one of the position sensor 422, 424, 426, 428 detects and generate the position signal indicating that the shoe storing shelf 104 has engaged with one of the corresponding tracks 232, 234. 236, 238, the controller 460 powers all the linear actuators 414 to move the shoe storing shelf 104 and other shoe storing shelves 104 in sequence along the path.

In an aspect of the present disclosure, the method 600 further includes generating, by the proximity sensor 488 located on one of the upper surface 312 of the first shoe retainer 314A and the second shoe retainer 314B, a proximity signal when the first shoe and the second shoe are inserted in the first shoe retainer 314A and the second shoe retainer 314B respectively. With the proximity sensor 488 located on one of the upper surface 312 of the first shoe retainer 314A and the second shoe retainer 314B, the proximity sensor 488 may detect insertion of the shoe in the respective one of the first shoe retainer 314A and the second shoe retainer 314B, and generate the proximity signal indicative thereof. The method 600 further includes receiving, by the controller 460, the proximity signal. The controller 460 being in signal communication with the proximity sensor 488 (as shown in FIG. 4B) may receive the proximity signal therefrom. The method 600 further includes transmitting, by the controller 460, power to turn on the ultraviolet lamp 486 located on the cross member 484 located above the shoe reception area 430 and angled such that ultraviolet light projects into the shoe cavity 430 and sterilizes the first shoe and the second shoe. That is, when it is confirmed that the shoes have been inserted in the shoe storing shelf 104 positioned in the shoe reception area 430 via the proximity signal, the controller 460 turn on the ultraviolet lamp 486 to sterilizes the first shoe and the second shoe therein. The method 600 further includes turning off, by the controller 460, the power to the ultraviolet lamp 486 after the predetermined time period. As discussed, the predetermined time period may be defined as a sufficient time period for completing sterilization of the shoe(s) by the ultraviolet light provided by the ultraviolet lamp 486. Therefore, the controller 460 may turn off the ultraviolet lamp 486 after the predetermined time period by breaking connection thereof with the power source 438, so as to not cause any wastage of power from the power source 438.

In an aspect of the present disclosure, the method 600 further includes receiving the shoe shelf identification code from the display 494 located on the keypad 492, the keypad 492 positioned on the central divider 220, when the pair of shoes is inserted into the first shoe storing shelf 104. That is, when the pair of shoes is inserted into the first shoe storing shelf 104, the controller 460 generates the shoe shelf identification code assigned to the first shoe storing shelf 104 and display the generated shoe shelf identification code on the display 494. The method 600 further includes storing, in the memory 262 of the controller 260, the shoe shelf identification code. That is, the generated shoe shelf identification code is stored in the memory 262. The method 600 further includes inputting the shoe shelf identification code into the keypad 292 when retrieving the pair of shoes. That is, the user may use the keypad 292 to input the shoe shelf identification code given to him/her, for retrieving his/her pair of shoes stored in the shoe organizer unit 100. The method 600 further includes matching, by the controller 460, the shoe shelf identification code to the shoe shelf identification code stored in the memory 262. That is, the controller 460 matches the inputted the shoe shelf identification code (via the keypad 292) with the shoe shelf identification code stored in the memory 262. The method 600 further includes providing, by the controller 460, power to each of the linear actuators 414 to move the shoe storing shelf 104 into the shoe reception area 430 of the shoe organizer unit 100. That is, if the inputted the shoe shelf identification code matches with the shoe shelf identification code stored in the memory 262, the controller 460 powers the linear actuators 414 to move the shoe storing shelves 104 along the path till the shoe storing shelf 104 corresponding to the matched shoe shelf identification code is positioned in the shoe reception area 430. The method 600 further includes removing the first shoe from the first shoe retainer 314A and the second shoe from the second shoe retainer 314B. That is, with the required shoe storing shelf 104 positioned in the shoe reception area 430, the user is able to access and can remove his/her shoes for retrieval from the shoe organizer unit 100.

In an aspect of the present disclosure, the method 600 further includes receiving a shoe shelf identification code card from the printer 496 located on the keypad 492 when storing the pair of shoes in the shoe organizer unit 100. That is, when the shoe shelf identification code is generated, a physical copy of the shoe shelf identification code card is dispensed by the printer 496 with the shoe shelf identification code printed thereon for reference of and perusal by the user. The method 600 further includes inputting the shoe shelf identification code card into the card receiving slot 498 in the keypad 492 when retrieving the pair of shoes from the shoe organizer unit 100. That is, instead of manually entering the shoe shelf identification code via the keypad 492 or the like, the user may simply input the dispensed (issued) shoe shelf identification code card into the card receiving slot 498. The controller 460 may read the shoe shelf identification code from the inputted shoe shelf identification code card itself.

Figure 8:
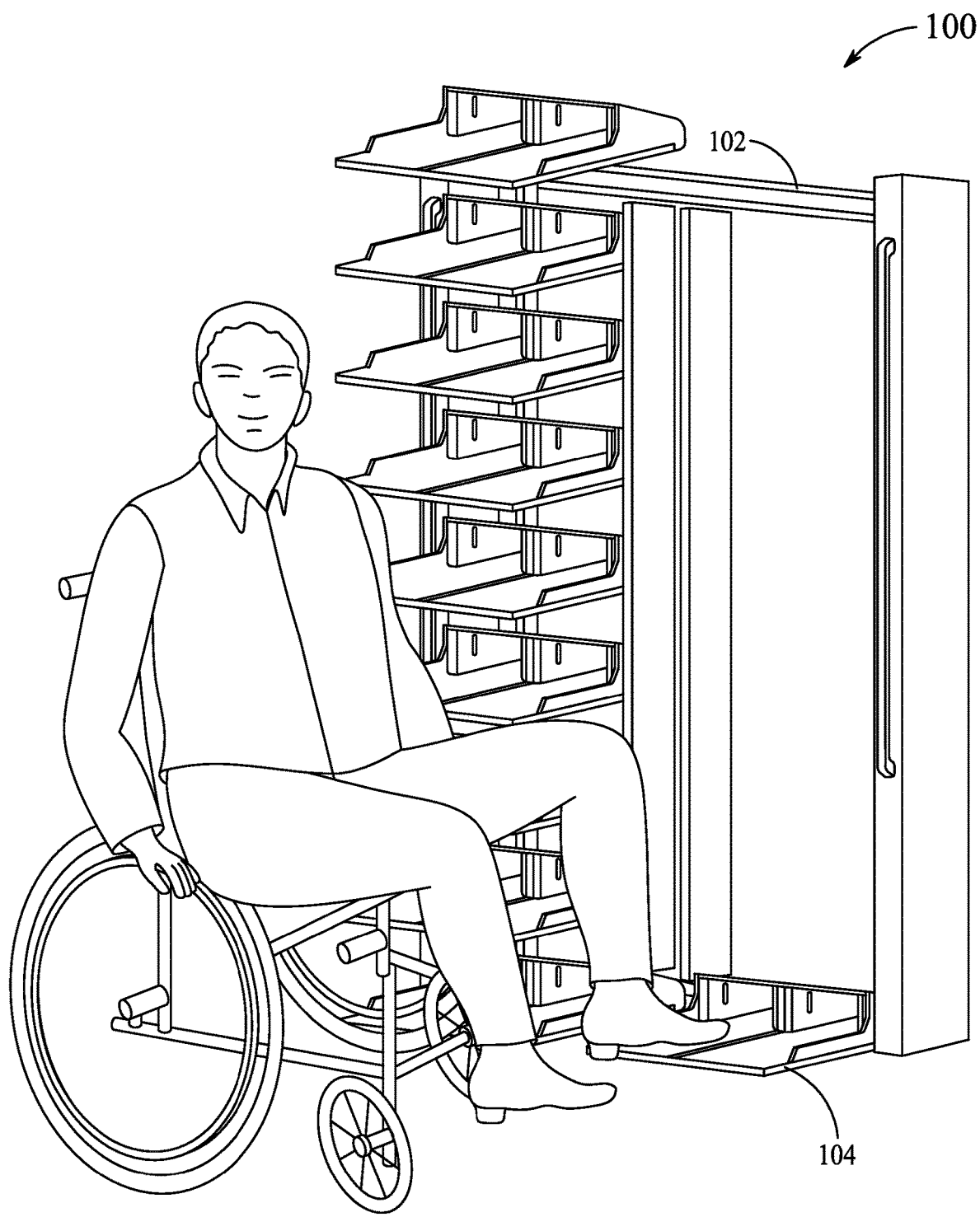
FIG. 8 is a diagrammatic illustration of the shoe organizer unit being used by a user with disability, according to certain embodiments.

Referring now to FIG. 8, a diagrammatic illustration of the shoe organizer unit 100 being used by a user with disability is illustrated. It may be contemplated that removing or putting on the shoes for a user with disability may be even more challenging. The shoe organizer unit 100 provides an unobstructed side reach and an unobstructed forward reach for such users, such as the user in a wheelchair as shown. The shoe organizer unit 100 makes it easier for the user with a disability to remove the shoes by simply inserting the feet with the shoes in the shoe storing shelf 104 and use the grip provided to the shoes thereby to pull his/her feet out from the shoes. Such use by press of a button (i.e., the actuator switch 452) can organize the shoes without needing to bend or stretch to find storage space therefore.

The first embodiment of the present disclosure is illustrated with respect to FIG. 1 through FIG. 8. The first embodiment describes the shoe organizer unit 100. The shoe organizer unit 100, comprising the cabinet 102, the cabinet 102 including the back wall 202 having the vertical axis 'Y' and the horizontal axis 'X', the cabinet top 204, the cabinet bottom 206, the first side wall 208 and the second side wall 210, the central divider 220, wherein the back wall 202 is separated into the first column 226 by the first side wall 208 and the central divider 220, and the second column 228 by the second side wall 210 and the central divider 220, the first vertical track 232 positioned on the first inner surface 212 of the first side wall 208, the second vertical track 234 positioned on the second inner surface 214 of the second side wall 210, the first horizontal track 236 positioned on the back wall 202 at a location above the cabinet bottom 206 along the horizontal axis 'X', the second horizontal track 238 positioned on the back wall 202 beneath the cabinet top 204 along the horizontal axis 'X', the plurality of shoe storing shelves 104, each shoe storing shelf 104 including the first projection 332 configured to engage with the first vertical track 232 and the second projection 334 configured to engage with the second vertical track 234, and the slider hook 336 configured to engage with either the first horizontal track 236 or the second horizontal track 238, the plurality of linear actuators 214 configured to move each one of the plurality of shoe storing shelves 104 in a path along the first vertical track 232, the first horizontal track 236, the second vertical track 234 and the second horizontal track 238, and the base surface 302 of each shoe storing shelf 104 divided into the left base surface 302A and the right base surface 302B, wherein each shoe storing shelf 104 includes the left shoe retainer 314A positioned on the left base surface 302A and the right shoe retainer 314B positioned on the right base surface 302B.

The left shoe retainer 314A includes the first pair of retractable pillars 318A, wherein each retractable pillar 318A is configured to retract in the outward direction when the shoe is inserted into the left shoe retainer 314A, wherein the retractable pillars 318A are configured to grip the shoe.

The right shoe retainer 314B includes the second pair of retractable pillars 318B, wherein each retractable pillar 318B is configured to retract in the outward direction when the shoe is inserted into the right shoe retainer 314B, wherein the retractable pillars 318B are configured to grip the shoe.

The shoe organizer unit 100 further comprising the textured rubber mat 322 located on the left base surface 302A and the right base surface 302B, wherein the textured rubber mat 322 is configured to provide friction when withdrawing the foot from the shoe.

Each retractable pillar 318A, 318B includes the elastic adjustable covering 320 configured to grip the sole of the shoe inserted between the retractable pillars 318A, 318B.

The shoe organizer unit 100 further comprising the shoe reception area 430 of the cabinet 102, wherein the shoe reception area 430 is located at the base 432 of the second column 228, the ultraviolet lamp 434 located on the base 432 of the second column 228, the ultraviolet lamp 434 positioned such that light generated by the ultraviolet lamp 434 shines into the shoe reception area 430, the proximity sensor 436 located in the shoe reception area 430, the power source 438 located within the central divider 220, the switch 440 operatively connected to the proximity sensor 436 and the ultraviolet lamp 434, wherein the switch 440 is configured to provide power from the power source 438 to the ultraviolet lamp 434 when the proximity sensor 436 detects the shoe storing shelf 104 in the shoe reception area 430, and the timer 442 connected to the switch, wherein the timer 442 is configured to turn off the switch 440 after the predetermined time period.

The shoe organizer unit 100 further comprising the first hand rail 240 located on the first front surface 216 of the first side wall 208 along the vertical axis 'Y', and the second hand rail 242 located on the second front surface 218 of the second side wall 210 along the vertical axis 'Y'.

The shoe organizer unit 100 further comprising the actuator switch 452 located on the front surface 230 of the central divider 220 at the location in the range of six inches to three feet above the cabinet bottom 206, wherein the actuator switch 452 is configured to generate the actuator switch signal when pressed, and wherein the plurality of linear actuators 214 is configured to move each shoe storing shelf 104 along the path from the current position on the path to the next position along the path upon receiving the actuator switch signal.

The shoe organizer unit 100 further comprising the actuator switch 452 located on the front surface 230 of the central divider 220 at the location in the range of six inches to three feet above the cabinet bottom 206, wherein the actuator switch 452 is configured to generate the actuator switch signal when pressed, and the plurality of position sensors 420, each position sensor operatively connected to the linear actuator, each position sensor configured to generate the position signal in response to sensing a presence of the shoe storing shelf 104 near its respective linear actuator, and the controller 460 located in the central divider 220 and operatively connected to receive the position signal from each position sensor and the actuator switch signal, the controller 460 including circuitry and the processor having program instructions configured to provide power to each of the linear actuators 414 to move the respective shoe storing shelf 104 along the path upon receiving the actuator switch signal.

The shoe organizer unit 100 further comprising the first transparent viewing window 472 covering the first front surface of the first column 226, the second transparent viewing window 474 covering the first portion of the second front surface of the second column 228, and the second portion of the second front surface of the second column 228 having the open area 430, wherein the open area 430 extends from the cabinet bottom 206 to two feet above the cabinet bottom 206, wherein the open area 430 is configured to provide access to the shoe storing shelf 104 located in the second column 228 on the cabinet bottom 206.

The shoe organizer unit 100 further comprising the first cross member 482 located at the cabinet top 204, the second cross member 484 located at the bottom of the second transparent viewing window 474, the ultraviolet lamp 486 located on the second cross member 484 such that ultraviolet light projects into the shoe cavity 430 when the ultraviolet lamp 486 is turned on, wherein the ultraviolet lamp 486 is operatively connected to the controller 460, the proximity sensor 488 located on one of the upper surface 312 of the left shoe retainer 314A and the right shoe retainer 314B, the proximity sensor 488 operatively connected to the controller 460, and wherein the controller 460 is configured to turn on the ultraviolet lamp 486 when the proximity sensor 488 detects the insertion of the shoe in either the left shoe retainer 314A or the right shoe retainer 314B and to turn off the switch 440 after the predetermined time period.

The shoe organizer unit 100 further comprising the keypad 492 located on the central divider 220 directly below the actuator switch 452, the keypad 492 configured to generate the shoe shelf identification code for each shoe storing shelf 104 located in the open area 430 and display the shoe shelf identification code, the memory 462 operatively connected to the controller 460, wherein the memory 462 is configured to receive the shoe shelf identification code, wherein the keypad 492 is further configured to receive the shoe shelf identification code input and transmit the shoe shelf identification code input to the controller 460, and wherein the controller 460 is further configured to match the shoe shelf identification code input to the shoe shelf identification code stored in the memory 462, identify the particular shoe storing shelf 104 associated with the shoe shelf identification code and provide power to the linear actuators 414 to move the particular shoe storing shelf 104 to the open area 430.

The second embodiment of the present disclosure is illustrated with respect to FIG. 1 through FIG. 8. The second embodiment describes the method 500 of using the shoe organizer unit 100 comprising storing the pair of shoes in the shoe organizer unit 100 by inserting the first shoe into the first shoe retainer 314A of the shoe storing shelf 104, wherein the shoe storing shelf 104 is located in the shoe reception area 430 of the shoe organizer unit 100; removing the first shoe by twisting the first shoe against the first pair of retractable pillars 318A located in the first shoe retainer 314A; inserting the second shoe into the second shoe retainer 314B of the shoe storing shelf 104; removing the second shoe by twisting the second shoe against the second pair of retractable pillars 318B located in the second shoe retainer 314B; receiving the shoe shelf identification code from the keypad 492 located on the shoe organizer unit 100, the keypad 492 operatively connected to the controller 460 which generates the shoe shelf identification code and stores the shoe shelf identification code in the memory 462; pressing the actuator switch 452 to move the shoe storing shelf 104 upwards into the sealed area of the shoe organizer unit 100; retrieving the pair of shoes from the shoe organizer unit 100 by inputting the shoe shelf identification code into the keypad 492, wherein the controller 460 matches the shoe shelf identification code to the shoe shelf identification code stored in the memory 462, the controller 460 further providing power to the plurality of linear actuators 214 to move the shoe storing shelf 104 into the shoe reception area 430 of the shoe organizer unit 100; and removing the first shoe from the first shoe retainer 314A and the second shoe from the second shoe retainer 314B.

The method 500 comprising twisting the first shoe against the first pair of retractable pillars 318A while holding the handrail 240, 242 located on the front wall 216, 218 of the cabinet 102.

The method 500 comprising receiving the shoe shelf identification code card from the printer 496 located on the keypad 492 when storing the pair of shoes in the shoe organizer unit 100; and inputting the shoe shelf identification code card into the card receiving slot in the keypad 492 when retrieving the pair of shoes from the shoe organizer unit 100.

The third embodiment of the present disclosure is illustrated with respect to FIG. 1 through FIG. 8. The third embodiment describes the method 600 for storing shoes in the plurality of shoe storing shelves 104 of the shoe organizer unit 100, the shoe organizer unit 100 including the cabinet 102, comprising moving, by the first linear actuator 402, the first shoe storing shelf 104 along the first horizontal track 236 from the base 432 of the first column 226 of the cabinet 102 to the shoe reception area 430 located at the base of the second column 228 of the cabinet 102; retracting the first linear actuator 402; inserting the first shoe into the first shoe retainer 314A of the first shoe storing shelf 104; removing the first shoe by twisting the first shoe against the first pair of retractable pillars 318A located in the first shoe retainer 314A, wherein the first pair of retractable pillars 318A are configured to press against the first shoe; inserting the second shoe into the second shoe retainer 314B of the first shoe storing shelf 104; removing the second shoe by twisting the second shoe against the second pair of retractable pillars 318B located in the second shoe retainer 314B, wherein the second pair of retractable pillars 318B are configured to press against the second shoe; raising the first shoe storing shelf 104 by the second linear actuator 404, wherein the first projection 332 located on the first side 308A of the first shoe storing shelf 104 engages with the fourth vertical track 235 located on the inner surface 224 of the central divider 220 of the cabinet 102, wherein the first plurality of shoe storing shelves 104 are vertically stacked one above the other in the second column 228 and are configured to sequentially move in the upward direction when the second linear actuator 404 raises each shoe storing shelf 104 in the shelf reception area 430 into the second column 228; moving the first support actuator 416 to support the first projection 332 located on the first side 308A of the first shoe storing shelf 104; retracting the second linear actuator 404, moving, by the third linear actuator 406, the top shoe storing shelf 104 of the first plurality of shoe storing shelves 104 upwards such that the slider hook 336 on the backside of the top shoe storing shelf 104 engages with the second horizontal track 238 located at the top of the second column 228; moving, by the fourth linear actuator 408, the top shoe storing shelf 104 from the second column 228 to the first column 226 to rest upon the second plurality of shoe storing shelves 104 which are vertically stacked one above the other in the first column 226 and which are configured to sequentially move in the downward direction in the first column 226; moving, by the fifth linear actuator 410, the top shoe storing shelf 104 downward such that the slider hook 336 on the backside of the top shoe storing shelf 104 disengages from the second horizontal track 238, wherein the bottom shoe storing shelf 104 of the first column 226 engages with the second support actuator 418; and when the first shoe storing shelf 104 is in the shoe reception area 430, releasing the second support actuator 418 and moving, by the sixth linear actuator 412, the bottom shoe storing shelf 104 of the first column 226 to engage with the first horizontal track 236.

The method 600 further comprising generating the actuation switch signal by the actuator switch 452 located on the front surface 230 of the central divider 220 at the location in the range of six inches to three feet above the cabinet bottom 206; generating the position signal at each linear actuator, by the plurality of position sensors 420, in response to sensing the presence of the shoe storing shelf 104 near its respective linear actuator; and receiving, by the controller 460 located in the central divider 220 between the first column 226 and the second column 228, the position signal from each position sensor and the actuator switch signal, the controller 460 including circuitry and the processor having program instructions configured to provide power to each of the linear actuators to move the respective shoe storing shelf 104 along upon receiving the actuator switch signal.

The method 600 further comprising generating, by the proximity sensor 488 located on one of the upper surface 312 of the first shoe retainer 314A and the second shoe retainer 314B, the proximity signal when the first shoe and the second shoe are inserted in the first shoe retainer 314A and the second shoe retainer 314B respectively; receiving, by the controller 460, the proximity signal; transmitting, by the controller 460, power to turn on the ultraviolet lamp 486 located on the cross member 484 located above the shoe reception area 430 and angled such that ultraviolet light projects into the shoe cavity 430 and sterilizes the first shoe and the second shoe; and turning off, by the controller 460, the power to the ultraviolet lamp 486 after the predetermined time period.

The method 600 further comprising receiving the shoe shelf identification code from the display 494 located on the keypad 492, the keypad 492 positioned on the central divider 220, when the pair of shoes is inserted into the first shoe storing shelf 104; storing, in the memory 462 of the controller 460, the shoe shelf identification code; inputting the shoe shelf identification code into the keypad 492 when retrieving the pair of shoes; matching, by the controller 460, the shoe shelf identification code to the shoe shelf identification code stored in the memory 462; providing, by the controller 460, power to each of the linear actuators 414 to move the shoe storing shelf 104 into the shoe reception area 430 of the shoe organizer unit 100; and removing the first shoe from the first shoe retainer 314A and the second shoe from the second shoe retainer 314B.

The method 600 further comprising receiving the shoe shelf identification code card from the printer 496 located on the keypad 492 when storing the pair of shoes in the shoe organizer unit 100; and inputting the shoe shelf identification code card into the card receiving slot in the keypad 492 when retrieving the pair of shoes from the shoe organizer unit 100.

Figure 9:
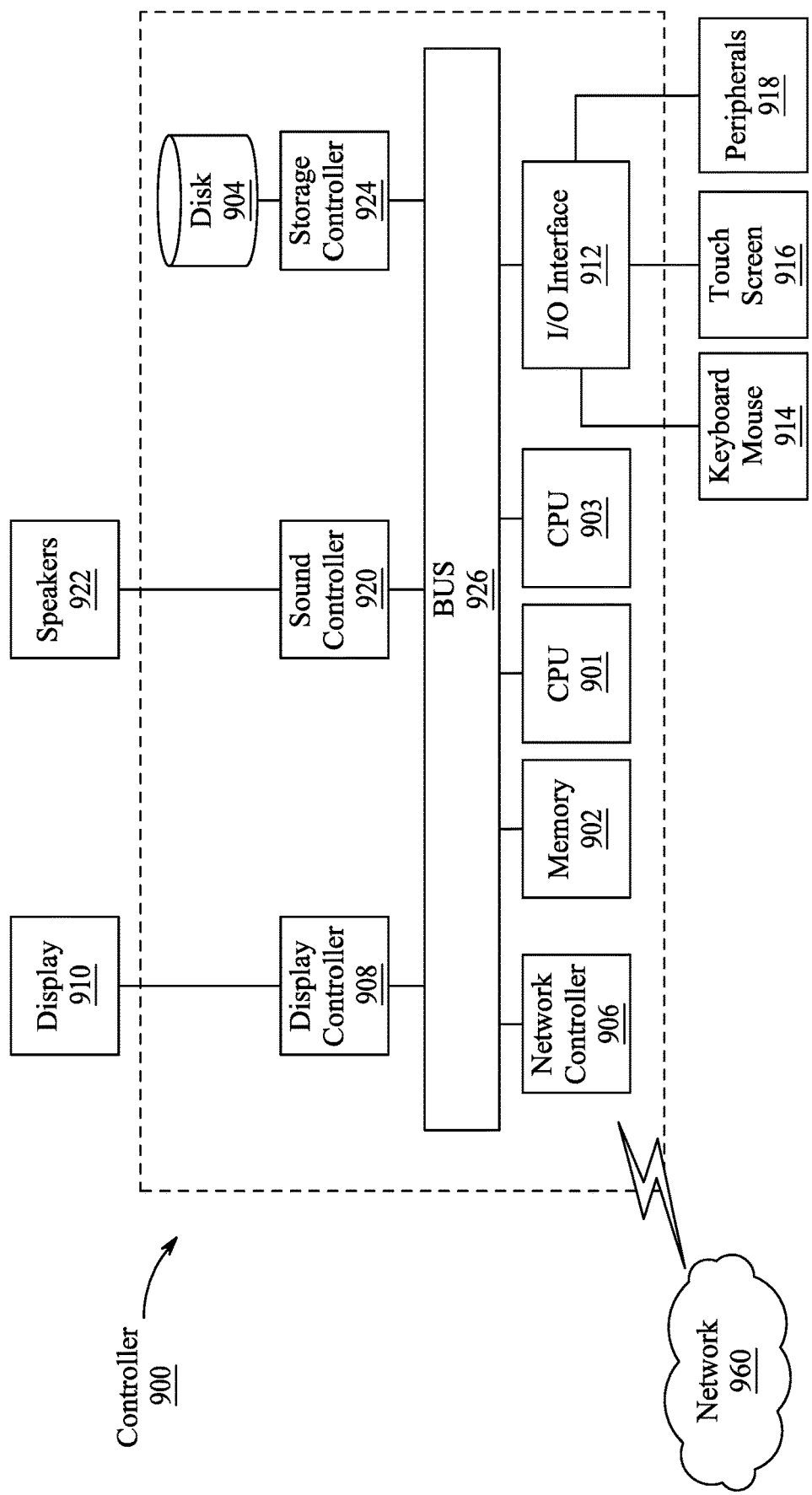
FIG. 9 is an illustration of a non-limiting example of details of computing hardware used in a computing system of the shoe organizer unit of FIG. 4A and FIG. 4B, according to certain embodiments.

Further details of hardware description of the controller of FIG. 4A and FIG. 4B according to exemplary embodiments is described with reference to FIG. 9. In FIG. 9, a controller 900 is described which is representative of the computing environment of FIG. 8 in which the controller 900 (also sometimes referred to as computing device) includes a CPU 901 which performs the processes described above/below. The process data and instructions may be stored in memory 902. These processes and instructions may also be stored on a storage medium disk 904 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 901, 903 and an operating system such as Microsoft Windows 7, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 901 or CPU 903 may be a Xenon or Core processor from Intel of America or an Opteron processor from AMD of America, or may be other processor types that would be recognized by one of ordinary skill in the art. Alternatively, the CPU 901, 903 may be implemented on an FPGA, ASIC, PLD or using discrete logic circuits, as one of ordinary skill in the art would recognize. Further, CPU 901, 903 may be implemented as multiple processors cooperatively working in parallel to perform the instructions of the inventive processes described above.

The computing device in FIG. 9 also includes a network controller 906, such as an Intel Ethernet PRO network interface card from Intel Corporation of America, for interfacing with network 960. As can be appreciated, the network 960 can be a public network, such as the Internet, or a private network such as an LAN or WAN network, or any combination thereof and can also include PSTN or ISDN sub-networks. The network 960 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 908, such as a NVIDIA GeForce GTX or Quadro graphics adaptor from NVIDIA Corporation of America for interfacing with display 910, such as a Hewlett Packard HPL2445w LCD monitor. A general purpose I/O interface 912 interfaces with a keyboard and/or mouse 914 as well as a touch screen panel 916 on or separate from display 910. General purpose I/O interface also connects to a variety of peripherals 918 including printers and scanners, such as an OfficeJet or DeskJet from Hewlett Packard.

A sound controller 920 is also provided in the computing device such as Sound Blaster X-Fi Titanium from Creative, to interface with speakers/microphone 922 thereby providing sounds and/or music.

The general purpose storage controller 924 connects the storage medium disk 904 with communication bus 926, which may be an ISA, EISA, VESA, PCI, or similar, for interconnecting all of the components of the computing device. A description of the general features and functionality of the display 910, keyboard and/or mouse 914, as well as the display controller 908, storage controller 924, network controller 906, sound controller 920, and general purpose I/O interface 912 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

Moreover, the present disclosure is not limited to the specific circuit elements described herein, nor is the present disclosure limited to the specific sizing and classification of these elements. For example, the skilled artisan will appreciate that the circuitry described herein may be adapted stand on changes on battery sizing and chemistry, or stand on the requirements of any intended back-up load to be powered.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A hands-free method of storing and retrieving footwear, comprising:
    storing a pair of shoes comprising a first shoe and a second shoe in the shoe organizer unit, by:
        inserting the first shoe of the pair of shoes into a first shoe retainer of a shoe storing shelf of a plurality of shoe storing shelves, wherein the shoe storing shelf is located in a shoe reception area of the shoe organizer unit;

removing the first shoe by twisting the first shoe against a first pair of retractable pillars located in the first shoe retainer;

inserting the second shoe of the pair of shoes into a second shoe retainer of the shoe storing shelf;

removing the second shoe by twisting the second shoe against a second pair of retractable pillars located in the second shoe retainer;

wherein the removing and the inserting of the first and second shoes are completed without using hands;

receiving a shoe shelf identification code from a keypad located on the shoe organizer unit, the keypad operatively connected to a controller which generates the shoe shelf identification code and stores the shoe shelf identification code in a memory;

pressing an actuator switch to move the shoe storing shelf upwards into a sealed area of the shoe organizer unit;

retrieving the pair of shoes from the shoe organizer unit by:

inputting the shoe shelf identification code into the keypad, wherein the controller matches the shoe shelf identification code to the shoe shelf identification code stored in the memory, the controller further providing power to a plurality of linear actuators to move the shoe storing shelf into a shoe reception area of the shoe organizer unit; and removing the first shoe from the first shoe retainer and the second shoe from the second shoe retainer.

2. The method of claim 1, comprising:

twisting the first shoe against the first pair of retractable pillars while holding a handrail located on a front wall of a cabinet.

3. The method of claim 2, comprising:

receiving a shoe shelf identification code card from a printer located on the keypad when storing the pair of shoes in the shoe organizer unit; and inputting the shoe shelf identification code card into a card receiving slot in the keypad when retrieving the pair of shoes from the shoe organizer unit.

* * * * *